(12) United States Patent
Bannister et al.

(10) Patent No.: US 10,751,335 B2
(45) Date of Patent: Aug. 25, 2020

(54) SIGNALING-BIASED MU OPIOID RECEPTOR AGONISTS

(71) Applicant: THE SCRIPPS RESEARCH INSTITUTE, La Jolla, CA (US)

(72) Inventors: Thomas D. Bannister, Palm Beach Gardens, FL (US); Laura M. Bohn, Jupiter, FL (US); Cullen L. Schmid, Cambridge, MA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/085,100

(22) PCT Filed: Mar. 15, 2017

(86) PCT No.: PCT/US2017/022552
§ 371 (c)(1),
(2) Date: Sep. 14, 2018

(87) PCT Pub. No.: WO2017/161017
PCT Pub. Date: Sep. 21, 2017

(65) Prior Publication Data
US 2019/0055214 A1    Feb. 21, 2019

Related U.S. Application Data

(60) Provisional application No. 62/308,333, filed on Mar. 15, 2016.

(51) Int. Cl.
*A61K 31/454* (2006.01)
*A61K 31/4166* (2006.01)
*C07D 401/04* (2006.01)
*A61P 29/02* (2006.01)

(52) U.S. Cl.
CPC ........ *A61K 31/454* (2013.01); *A61K 31/4166* (2013.01); *A61P 29/02* (2018.01); *C07D 401/04* (2013.01)

(58) Field of Classification Search
CPC .................... A61K 31/4166; A61K 31/454
USPC ..................................................... 514/322
See application file for complete search history.

(56) References Cited

U.S. PATENT DOCUMENTS 7,244,744 B2 *  7/2007  Gross ................. A61K 31/00
                                                      514/322

FOREIGN PATENT DOCUMENTS

WO    WO-0107050 A1    2/2001
WO    WO-2017161017 A1    9/2014

OTHER PUBLICATIONS

Anderson, Chemistry & Biology (2003), vol. 10, pp. 787-797. (Year: 2003).*

(Continued)

*Primary Examiner* — Craig D Ricci
*Assistant Examiner* — Janet L. Coppins
(74) *Attorney, Agent, or Firm* — Schwegman Lundberg & Woessner, P.A.

(57) ABSTRACT

The invention provides—opioid receptor agonists that are analgesic agents and that promote diminished side effects relative to a comparably effective dose of morphine. The side effects that are absent or attenuated include one or more of the following: constipation, respiratory depression, tolerance, dependence, nausea, confusion, sedation, hypotension, and post-treatment withdrawal symptoms.

6 Claims, 10 Drawing Sheets

(56) References Cited

OTHER PUBLICATIONS

Shi et al;, Organic Letters (2003), vol. 5(5), pp. 633-636. (Year: 2003).*
Thiel, Nature Biotechnology (2004), vol. 22(5), pp. 513-519. (Year: 2004).*
Jong et al, Bioorganic & Medicinal Chemistry Letters (2004), vol. 14, pp. 181-185. (Year: 2004).*
"International Application Serial No. PCT/US2017/022552, International Preliminary Report on Patentability dated Sep. 27, 2018", 11 pgs.
"International Application Serial No. PCT/US2017/022552, International Search Report dated Jun. 8, 2017", 5 pgs.
"International Application Serial No. PCT/US2017/022552, Written Opinion dated Jun. 8, 2017", 9 pgs.
Jong, Ling, et al., "The design and synthesis of a novel quinolizidine template for potent opioid and opioid receptor-like (ORL1, NOP) receptor ligands", Bioorgan IC & Medicinal Chemistry Letters, Pergamon, Amsterdam, NL, vol. 14, No. 1, (Jan. 1, 2004), 181-185.
Kawamoto, Hiroshi, et al., "Discovery of the first potent and selective small molecule opioid receptor-like (ORL1) antagonist:1-A(3R,4R)-1-cyclooctylmethyl-3-hydroxymet hyl-4-piperi dyIÜ-3-ethyl-1,3-dihydro-2H-be nzimidazol-2-one (J-113397)", Journal of Medicinal Chemistry, American Chemical Society, vol. 42, No. 25, (Dec. 16, 1999), 5061-5063.
Kenakin, Terry, et al., "A Simple Method for Quantifying Functional Selectivity and Agonist Bias", ACS Chemical Neuroscience, vol. 3, No. 3, (Mar. 21, 2012).
Poulain, Rébecca, et al., "From hit to lead. Analyzing Structure-profile relationships", Journal of Medicinal Chemistry, American Chemical Society, vol. 44, (Sep. 11, 2001), 3391-3401.

* cited by examiner

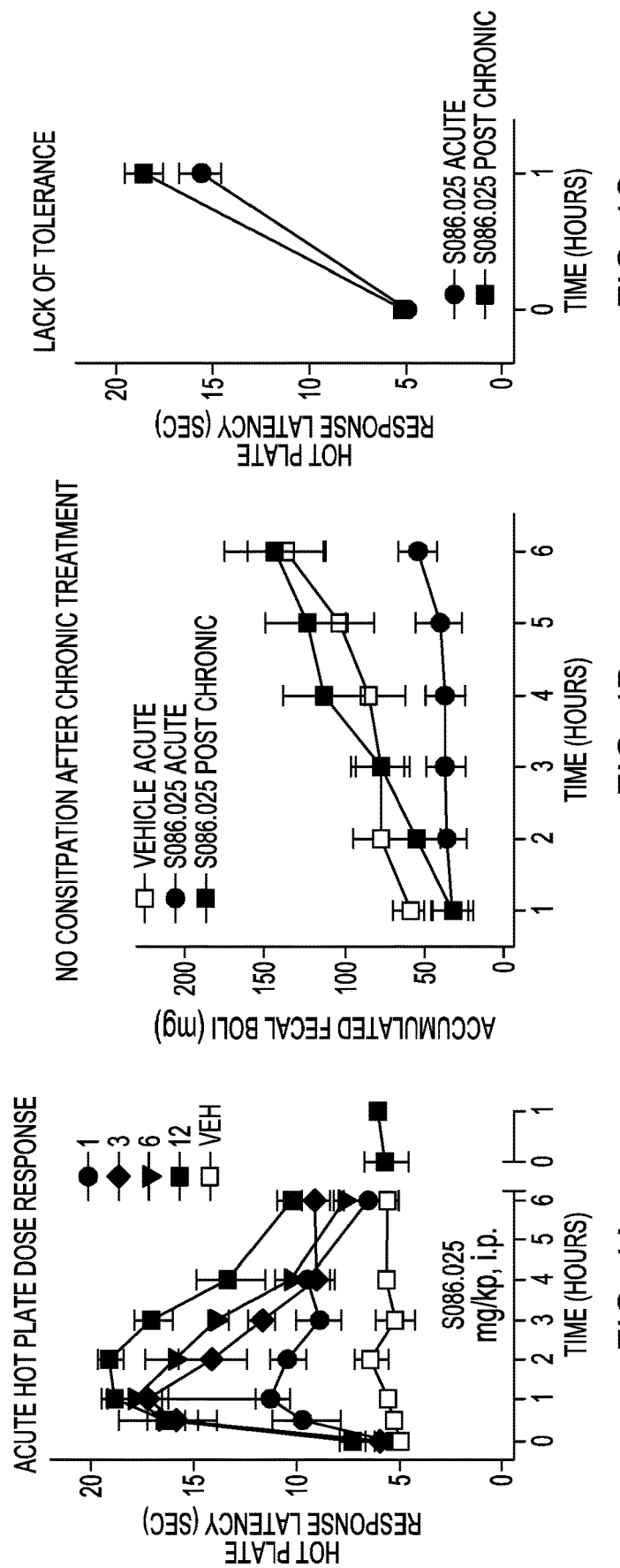

IV and PO dosing:

Morphine Sulfate

| IV 1 mg/kg | MS | ± | SEM |
|---|---|---|---|
| $T_{1/2}$ (hr) | 3.04 | ± | 0.03 |
| $T_{max}$ (hr) | 0.08 | ± | 0.00 |
| $C_{max}$ (ng/mL) | 239 | ± | 4 |
| $C_{max}$ (µM) | 0.32 | ± | 0.00 |
| $AUC_{last}$ (min*ng/mL) | 11083 | ± | 523 |
| $AUC_{last}$ (µM.hr) | 0.24 | ± | 0.01 |
| $AUC_{INF\_obs}$ (min*ng/mL) | 11715 | ± | 577 |
| $AUC_{\%Extrap}$ | 5.38 | ± | 0.20 |
| Cl_obs (mL/min/kg) | 85.77 | ± | 4.18 |
| $MRT_{INF\_obs}$ (hr) | 1.64 | ± | 0.04 |
| Vss_obs (L/kg) | 8.42 | ± | 0.22 |

FIG. 8C

| PO 3 mg/kg | MS | ± | SEM |
|---|---|---|---|
| $T_{1/2}$ (hr) | 7.32 | ± | 2.57 |
| $T_{max}$ (hr) | 0.08 | ± | 0.00 |
| $C_{max}$ (ng/mL) | 54 | ± | 8 |
| $C_{max}$ (µM) | 0.07 | ± | 0.01 |
| $AUC_{last}$ (min*ng/mL) | 4242 | ± | 208 |
| $AUC_{last}$ (µM.hr) | 0.09 | ± | 0.00 |
| $AUC_{INF\_obs}$ (min*ng/mL) | 6483 | ± | 584 |
| $AUC_{\%Extrap}$ | 33.13 | ± | 8.14 |
| Cl_obs (mL/min/kg) | 469.82 | ± | 39.24 |
| F% | 13 % | | |

FIG. 8D

IV and PO dosing:

S186.005

| IV 1 mg/kg | S186.005 | ± | SEM |
|---|---|---|---|
| $T_{1/2}$ (hr) | 8.66 | ± | 0.81 |
| $T_{max}$ (hr) | 0.08 | ± | 0.00 |
| $C_{max}$ (ng/mL) | 988 | ± | 82 |
| $C_{max}$ (µM) | 2.17 | ± | 0.18 |
| $AUC_{last}$ (min*ng/mL) | 95771 | ± | 3319 |
| $AUC_{last}$ (µM.hr) | 3.51 | ± | 0.12 |
| $AUC_{INF\_obs}$ (min*ng/mL) | 185279 | ± | 15465 |
| $AUC_{\%Extrap}$ | 47.66 | ± | 4.17 |
| Cl_obs (mL/min/kg) | 5.47 | ± | 0.45 |
| $MRT_{INF\_obs}$ (hr) | 11.30 | ± | 1.37 |
| Vss_obs (L/kg) | 3.64 | ± | 0.19 |

FIG. 8E

| PO 3 mg/kg | S186.005 | ± | SEM |
|---|---|---|---|
| $T_{1/2}$ (hr) | 9.14 | ± | 1.13 |
| $T_{max}$ (hr) | 2.00 | ± | 0.00 |
| $C_{max}$ (ng/mL) | 423 | ± | 22 |
| $C_{max}$ (µM) | 0.93 | ± | 0.05 |
| $AUC_{last}$ (min*ng/mL) | 147309 | ± | 9372 |
| $AUC_{last}$ (µM.hr) | 5.39 | ± | 0.34 |
| $AUC_{INF\_obs}$ (min*ng/mL) | 361362 | ± | 46486 |
| $AUC_{\%Extrap}$ | 58.26 | ± | 4.02 |
| Cl_obs (mL/min/kg) | 8.63 | ± | 1.27 |
| F% | 51 % | | |

FIG. 8F

SIGNALING-BIASED MU OPIOID RECEPTOR AGONISTS

CLAIM OF PRIORITY

This application claims the benefit of priority to U.S. Provisional Application Ser. No. 62/308,333, filed Mar. 15, 2016, which is herein incorporated by reference in its entirety.

STATEMENT OF GOVERNMENT SUPPORT

This invention was made with government support under R01DA033073 awarded by the NIH-NIDA. The U.S. government has certain rights in the invention.

BACKGROUND

Current available therapies for the management of severe pain, in its many forms, are largely inadequate. Acute pain, which typically persists for less than a month and is associated with a direct cause, such as tissue damage resulting from injury or surgery, can be distinguished from chronic pain, which is longer-lasting, occurring over months or years. Many chronic pain sufferers are especially poorly treated or are undertreated, which negatively impacts their quality of life and contributes to an inability to work, emotional distress, mood disorders, disrupted social integration and depression. Chronic pain often is characterized by short term episodic recurrences followed by an eventual relapse, only to later emerge again. Thus shorter-term treatments that are appropriate for acute pain therapy can be used with some success for chronic pain therapy when given in the midst of an episodic recurrence.

Opioids have been used to treat severe pain since antiquity. They remain the major class of pain relievers used today to treat post-surgical and cancer pain, largely due to of their effectiveness and rapid onset of pain relief. The opioid class of pain relievers interacts with specific receptors in the brain that are also found outside the CNS. The opioid family of receptors includes the mu ($\mu$), kappa ($\kappa$) and delta ($\delta$) receptors as well as the nociceptin receptor, also called the orphanin or ORL-1 receptor. Molecules that interact with these receptors have been classified by their ability to promote or block receptor signaling, and are commonly termed full agonists, partial agonists, mixed agonist-antagonists, or antagonists, depending upon the nature and consequence of their physical interactions with one or more of these receptors. The most effective opioid pain relievers are full agonists or partial agonists of either the $\mu$ or $\kappa$ receptors, with $\mu$ receptor agonists (termed MOR agonists, for mu opioid receptor) most often used. For comprehensive reviews on the opioid receptors as analgesic targets see (1-3).

Opioid receptor agonists are most often used for treating severe and ongoing pain in humans and/or other mammals. Opioid analgesics that are effective in humans also produce antinociception in rodent laboratory models. Antinociception is defined as the blockade of the perception of a nociceptive stimulus, wherein a nociceptive stimulus is defined as one conferring "somatic or visceral pain processed by a normal, unaltered nervous system" (4). Two traditional tests of antinociception in mice and rats are the "hot plate" and "tail flick" assays, wherein the response latency following exposure to an uncomfortable thermal stimulus is monitored. Antinociception is evident when the test drug induces an extension of latency of response to the stimulus that proves to be significantly greater than the latency of the basal response. The hot plate test involves limited exposure of the paw pads to a heated surface and the animal is monitored for the time it takes to remove its paws from the surface. The tail flick test involves exposing the tail to a thermal stimulus and the latency for movement from the heat source of the tail is measured.

All marketed MOR agonists (e.g., morphine, oxycodone, meperidine, methadone, levorphanol, fentanyl), while effective in therapy for many types of pain, cause several unwanted side effects. These include constipation, respiratory depression, nausea, confusion, sedation, hypotension, development of tolerance (i.e., requiring higher and higher doses over time to maintain effective pain relief), dependence, and the prevalence of post-treatment withdrawal symptoms. Each of these effects contributes to an underutilization of these pain relievers for effective pain therapy. Often a minimum dose that is required to achieve adequate pain relief is near to the minimum dose that is required to elicit unwanted and possibly deadly side effects. This relationship, commonly termed a safety index or therapeutic window, differs significantly within the patient population. Its narrowness requires constant monitoring of patients receiving these drugs for signs of side effects, particularly those that are life-threatening (respiratory failure, as an example). Thus the duration of hospital stays is significantly increased for hospitalized patients treated with MOR agonists, with discharge often being delayed until doses of administered drug can be significantly lowered to the point at which normal bowel movements, signs of normal respiration and evidence of normal cognitive function become apparent.

The unwanted side effects of MOR agonists can be addressed to some extent by very careful dose titration and close patient monitoring. Morphine is often used as the opioid pain reliever of choice, for several reasons. It is relatively inexpensive and it has very well-characterized pharmacokinetics and pharmacodynamics that suggest doses for which the target therapeutic window is likely to be reached. Often, however, the necessary dose titration may take many hours or even days to establish, with inadequate pain relief obtained in the interim. Higher doses may be required following the onset of tolerance. The respiratory depression and constipation issues are perhaps the areas of highest concern, as the former can result in fatal overdose and the latter may be severe, debilitating, and require extended hospitalization or even require surgical intervention. Physical dependence is also a concern in long-term opioid therapy, as cessation of opioid drug administration may lead to apathy, weight loss, insomnia, anxiety, sexual dysfunction, and overwhelming drug cravings (1, 3). Dependence and addiction also contribute to societal concerns, such as compromised public safety owing to opiate-related crime.

The balance of the different $\mu$-opioid-induced side effects differs slightly among known MOR agonists, but all such therapies have inherent risks. The severity of the side effects encountered are also generally proportional to the degree of pain relief provided by these drugs, which led to a simplistic model that viewed receptors as similar to an on/off switch, wherein an 'on' mode is characterized by receptor agonism (either full or partial) and an 'off' mode is characterized either by a lack of receptor agonism or by receptor antagonism. This model largely excluded the notion that the pain relieving properties of any opioid drug can theoretically be dissociated from one or more of its possible side effects. The model held that one switch, turned on, must result in a constellation of both positive and negative effects.

In recent years the physical structure of the MOR has been determined by X-ray techniques (5). Even prior to this achievement, the complexity of MOR signaling was becoming more apparent. There is not just one cascade of events, or signal, conveyed upon binding of a MOR agonist, but several. These downstream events include G protein coupling, adenylyl cyclase inhibition, receptor phosphorylation, βarrestin recruitment, and receptor internalization, events coordinated by regulatory proteins whose activity is dependent upon receptor activation (for reviews see (1, 6)). Small differences in the degree of activation of these different pathways may account for the slight differences in the side effect profiles among the different known MOR agonists. In addition, location of receptors, such as those on certain nerve terminal versus those in peripheral sites may also contribute to the side effect profiles. Drug potency and efficacy has usually been measured in vitro using assays for G protein coupling and for adenylyl cyclase inhibition. Assays measuring other downstream events, however, are not always in agreement with such potency assessments for certain MOR agonists.

Different G protein-coupled receptor agonists can in fact trigger distinct receptor signaling pathways. This phenomenon has been termed "functional selectivity", "ligand-directed signaling", "biased agonism" and "collateral efficacy" by the pharmacology community; such insights are strongly impacting new approaches in drug discovery (7-12). This concept is based on the idea that the chemical characteristics of the ligand may alter the conformation of the receptor such that it will interact preferentially with certain cellular proteins to mediate distinct biological responses. Therefore, the properties of the ligand bound dictate the nature of the receptor-protein interactions. Currently, marketed MOR agonists do not display significant functional selectivity. Moreover, there exists no a priori reason why such selectivity would not be possible. If different receptor signaling pathways ultimately lead to the manifestation of different side effects, a functionally selective MOR agonist can in principle be a potent pain relieving agent with an altered side effect profile, with one or more side effects being diminished or even nonexistent.

Over a decade ago the Bohn Lab began studying mice lacking GPCR regulatory proteins and found that mice with a genetic deletion of βarrestin2 display enhanced and prolonged morphine-induced antinociception (13-18). βArrestin2 is a scaffolding protein that can ad as a desensitizing element or as a signal transduction facilitator. Studies in the Bohn group have shown that morphine-induced analgesia is enhanced while tolerance is attenuated in mice lacking βarrestin2. Other studies in the Bohn group show that the severity of certain side effects, including physical dependence, constipation, and respiratory suppression are significantly reduced in mice lacking βarrestin2 (11, 14, 17-20). This suggests that in at least some organ systems and brain regions, βarrestin2 facilitates MOR signaling, that βarrestin2 plays a key role in determining MOR responsiveness, and that it serves as a critical switch in determining some of morphine's many effects. Therefore, agonists that could activate G protein-mediated signaling of the mu opioid receptor without inducing interactions with βarrestin2 would be a new class of potent pain relieving agents that should display fewer side effects. Such MOR agonists will promote antinociception, and based upon the animal model, should promote less respiratory suppression, dependence, tolerance and/or constipation. Since the publication of these findings and the realization of the possible therapeutic implications, attempts to discover such ligands have been a major interest within the pharmaceutical research community (21). The first such disclosed compound, TRV-130 (from Trevena, Inc.) is a "biased" MOR agonist and as of this writing is soon scheduled to enter Phase 2 clinical trials (22-24).

The desire to quantify functional selectivity has given rise to several mathematical models, all of which have been initially based on the Black and Leff operational model (Nobel Prize, 1988) (25). Development of this model has led to a means of simultaneously comparing the response that an agonist can elicit in one assay to the response elicited in another by normalizing its relative efficacy and potency to the performance a reference agonist that is run in parallel in both assays. Using the operational model allows one to simultaneously compare relative potencies and efficacies within an assay relative to the performance of a reference agonist, when properly normalized to minimize the contribution that differences in assay methodologies may impart. The relative efficiency of an agonist's ability to perform with respect to individual functions can then be compared. Reference compounds must be routinely used as comparators so that the potency and efficacy differences are not greatly influenced by inter-assay variation.

This usefulness of bias calculations is illustrated by the following example comparing relative potencies of an opioid enkephalin analog ([D-Ala2, N-MePhe4, Gly-ol]-enkephalin, "DAMGO") and morphine in selected assay formats. In a βarrestin2 recruitment assay using a commercial enzyme fragment complementation protocol, DAMGO and morphine showed $EC_{50}$ values of 217 and 361 nM, respectively. When an alternative βarrestin2-MOR assay was used, a bioluminescent resonance energy transfer (BRET) methodology, $EC_{50}$ values of 19 nM (DAMGO) and 46 nM (morphine) nM were obtained (26). While the absolute values reported are markedly different in the two assay systems, the relative potency is in general agreement. A similar trend is seen in results of a G protein coupling assay, where DAMGO was shown to be roughly 2 fold more potent ($EC_{50}$ values of 20 nM for DAMGO, 43 nM for morphine). In comparison to DAMGO, morphine is generally less efficient across assays; i.e., it is a partial agonist in both systems with a lower potency for stimulating both responses. Upon mathematical application of the operational model to both systems, normalized to the performance of DAMGO in both assays, one would calculate a "bias factor" of 1 for DAMGO (it is performing in par with itself) and a value approaching 1 for morphine (in our hands this value is 1.07). A truly biased ligand significantly diverges from 1, reflecting its ability to act on par with DAMGO in one assay, but less (or more) efficiently in another (27).

SUMMARY

In the context of this invention, a G protein bias factor substantially greater than 1 indicates a preference for ligands to promote G protein coupling over βarrestin2 recruitment. In our experience, there is a certain degree of error that is introduced in determining bias factors such that the confidence intervals (95%) surrounding the calculation of bias can lead to an error range that encompasses 1. A compound for which the degree of bias is determined to be 1.5, for example, with $CI_{95\%}$ (0.9-2.1), may not be truly biased. Therefore we have focused on compounds with a calculated bias factor significantly greater than 1, and preferably with a bias factor that is above 3.0. The mathematical equation used to calculate the bias factor is described in the literature (25, 27). Nonlinear regression analysis, fitting to these equations, was performed using GraphPad Prism 6.0 software (27-29).

Compounds meeting such a high threshold for promoting G protein signaling over βarrestin2 recruitment may be expected to have measurable differences in their effects in vivo, if such effects are differentially linked to these two differing MOR activation pathways. We propose that compounds that are significantly biased for G protein signaling over βarrestin2 recruitment (G/βarr2 bias factors >1.0) and that are potent agonists in G protein signaling assays will effectively attenuate pain perception. Further, at a dose at which pain relief is provided, side effects which are mechanistically linked to βarrestin2 recruitment will be less severe or possibly even absent. Moreover, we propose that compounds with a G/βarr2 bias factor over 3.0 will be able to elicit, in vive, desired G protein signaling-derived effects (decreased pain perception) with further diminishment of one or more of the accompanying side effects that are mechanistically linked to βarrestin2 recruitment.

While most of the background data and emerging clinical evidence suggests that signaling bias for G coupling and against βarrestin2 recruitment may be the most important factor in expanding the therapeutic window of a functionally biased opioid, other events upstream to βarrestin2 recruitment, such as phosphorylation of the receptor, may also be important. Therefore, agonists that prompt phosphorylation of different residues on the receptor, relative to conventional mu agonists, may result in the lack of βarrestin2 recruitment in the cellular context. Thus in vivo a difference in phosphorylation profile prompted by agonist treatment may confer the desired expansion of the therapeutic window. Therefore, βarrestin2 recruitment assays are a means of monitoring the signaling differences afforded by new ligands, relative to reference agonists, in a broad sense.

Based on the evidence reported in this invention, and the emerging clinical evidence (23, 24), the bias factor of a MOR agonist may be useful for predicting its safety index. The bias factor calculated for the most biased MOR ligand reported to date, TRV-130, in our hands is 3.0 (for G/βarr2). A dose separation efficacy of TRV-130 for antinociception and respiratory suppression as well as constipation in rodent models has been reported (22).

No information in the existing literature suggests how such signaling bias may be predictably obtained in any structural series or how much bias will be necessary to translate into clinical relevance. No highly G/βarr2 biased MOR agonists (bias factor >3.0) have, to our knowledge, been disclosed to date.

One aspect of the present invention relates to novel heterocyclic compounds. Additional aspects of the present invention relate to the use of the novel heterocyclic compounds as functionally selective agonists for opioid receptors. Additional aspects of the present invention relate to the use of these novel functionally selective heterocyclic opioid agonists as pain relieving agents. Another aspect of the present invention relates to the use of these novel functionally selective heterocyclic opioid agonists as pain relieving agents for the treatment of chronic or acute pain in humans, with a more tolerable side effect profile relative to existing agents such as morphine.

A scaffold of particular interest, because individual appropriately-substituted compounds in the series display high potency and high G/arr2 bias, is the N-benzyl piperidine 4-benzimidazolone series (FIG. 1). Compounds in this series, broadly defined, have been reported to be MOR agonists in the past (30). Moreover, compounds in this series have also been developed for a number of other indications, making the scaffold known as a privileged scaffold for GPCR binding (31-33), and a chemotype whose members tend to have favorable drug-like properties (34, 35), which is of high importance in the design of functionally biased MOR agonists.

BRIEF DESCRIPTION OF THE FIGURES

FIG. 4 is a graphic representation of the data obtained in Example 32, showing antinociception and constipation induced by compound S086.025 (the product of Example 3), following acute and following chronic administration.

DETAILED DESCRIPTION

Figure 1:
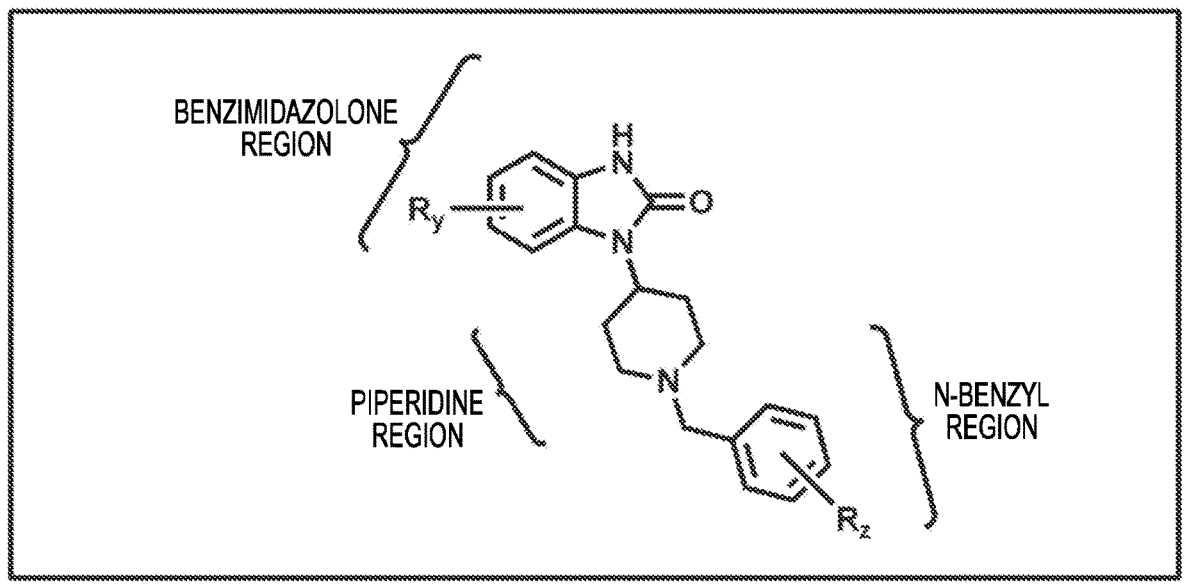
FIG. 1 depicts the overall structural design strategy of compounds of the present invention.

The following discloses various embodiments of the present invention, chemical compounds and compositions and therapeutic methods of use thereof.

Embodiment 1

A compound of structure 1 with suitable substituents $R^1$-$R^8$, specified as follows.

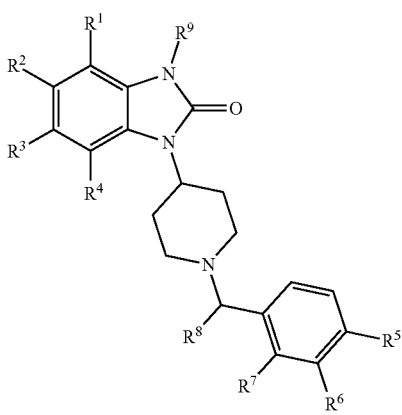

1) One or more groups $R^1$-$R^4$ is not a hydrogen atom.
2) One or more groups $R^5$-$R^7$ is also not a hydrogen atom.
3) $R^1$, $R^2$, $R^3$, and $R^4$ independently=H, Cl, Br, F, $OCF_3$, Me, lower alkyl.
4) $R^5$=H, Cl, Br, F, Me, $CF_3$, $OCF_3$, $OCHF_2$, $OCH_2F$, OMe, O-alkyl, SMe, S-alkyl, NH-acyl, N(Me)-acyl, phenyl, aryl, heteroaryl, O-phenyl, O-aryl, O-heteroaryl; wherein the phenyl, aryl, heteroaryl, O-phenyl, O-aryl, or O-heteroaryl groups may be substituted with one or more groups among F, Cl, Me, $CF_3$, and lower alkyl.
5) $R^6$=H, Cl, Br, F, Me, Et, lower alkyl, $CF_3$, $OCF_3$, $OCHF_2$, $OCH_2F$, OMe, O-alkyl, SMe, S-alkyl, NH-acyl, N(Me)-acyl, phenyl, aryl, heteroaryl, O-phenyl, O-aryl, O-heteroaryl; wherein the phenyl, aryl, heteroaryl, O-phenyl, O-aryl, or O-heteroaryl groups may be substituted with one or more groups among F, Cl, Me, $CF_3$, and alkyl. In cases where $R^5$ and $R^6$ both are O-alkyl they may be connected together in a ring of 5-7 atoms using 1-3 $CH_2$ groups.
6) $R^7$=Cl, Br, F, Me. $CF_3$, $OCF_3$, $OCHF_2$, $OCH_2F$.
7) $R^8$=H, Me, Et (including all stereoisomers).
8) $R^9$=H, Me, Et, lower alkyl, $CH_2$-cycloalkyl.

Also encompassed are all pharmaceutically acceptable salt forms, hydrates, solvates, and polymorphic crystalline forms thereof, as well as amorphous forms thereof. All stereoisomeric and isotopic forms are also encompassed.

Embodiment 2

A compound of embodiment 1 that shows mathematically defined functional selectivity, displaying bias for G protein signaling over βarrestin2 recruitment or receptor phosphorylation profiles, wherein functional selectivity with respect to arrestin2 recruitment bias is defined as having a G/βarr bias factor >1.0, with the G protein signaling efficiency is assessed using a standard $[^{35}S]GTPγS$ binding assay, as described herein.

Embodiment 3

A compound of embodiment 1 that shows significant and unexpected bias for G protein signaling, having a G/βarr bias factor >3.0, with the G protein signaling efficiency is assessed using a standard $[^{35}S]GTPγS$ binding assay, as described herein.

Embodiment 4

A compound of embodiment 1 that shows significant and unexpected bias for G protein signaling, having a G/βarr bias factor >9.0, with the G protein signaling efficiency is assessed using a standard $[^{35}S]GTPγS$ binding assay, as described herein.

Embodiment 5

A compound of any one of embodiments 2-4 that shows significant effects upon pain perception in humans and/or other mammals.

Embodiment 6

A compound of embodiment 5 in a suitable pharmaceutical formulation for use in humans and/or other mammals.

Embodiment 7

A compound of embodiment 1, wherein the compound is any of the following compounds, including all stereoisomeric forms, all isotopic forms, all crystalline and amorphous forms, and all pharmaceutically acceptable salt forms thereof:

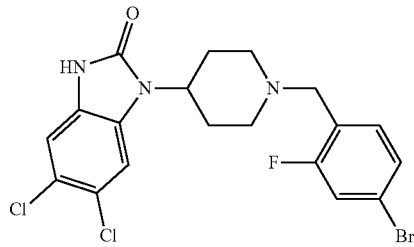

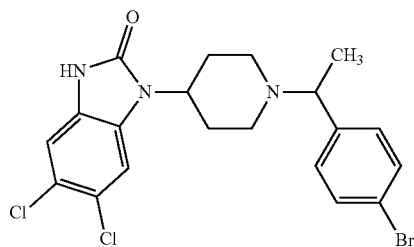

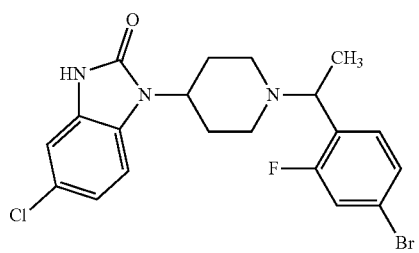

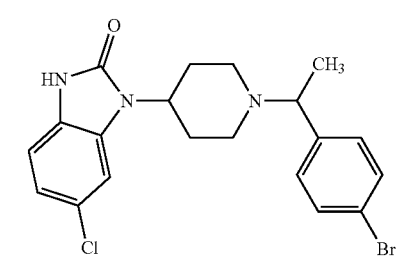

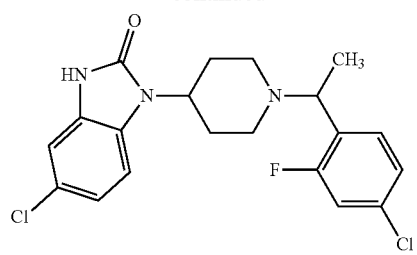
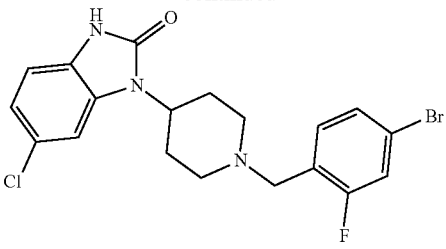
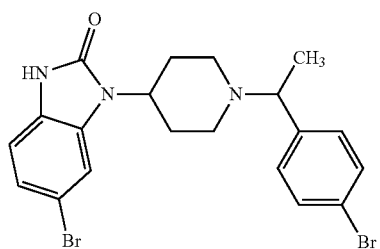
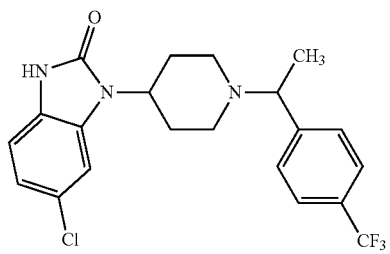
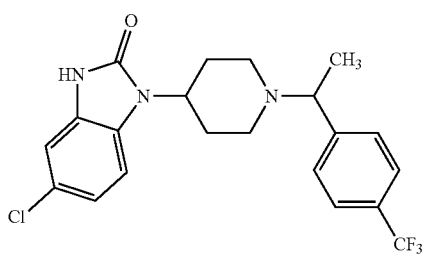
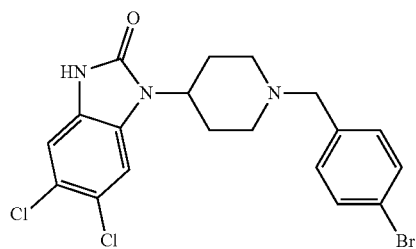
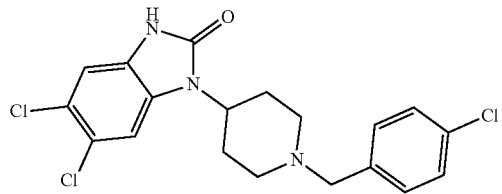
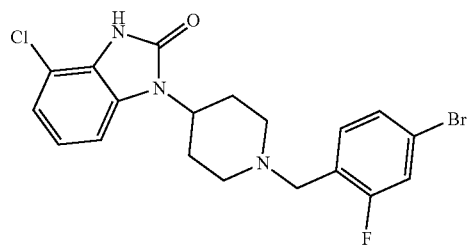

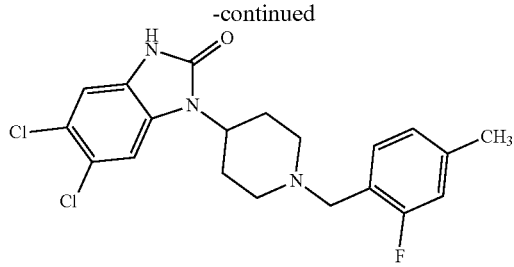

Embodiment 8

A pharmaceutical composition comprising a compound of any one of embodiments 1-7 and a pharmaceutically acceptable excipient.

Embodiment 9

A compound of any one of embodiments 1-7 for treatment of pain in a mammal.

Embodiment 10

A method of treatment of pain in a mammal, comprising administering to the mammal an effective dose of the compound of any one of embodiments 1-7.

Embodiment 11

The method of embodiment 10, wherein the mammal is a human.

Embodiment 12

The method of embodiment 11 wherein the pain is chronic pain or acute pain.

Embodiment 13

The method of embodiment 10 wherein the compound promotes antinociception, with fewer or diminished side effects, relative to a dose of morphine that promotes a comparable degree of antinociception.

Embodiment 14

The method of embodiment 13, wherein the side effects that are absent or attenuated in the treated patient include one or more of the following: constipation, respiratory depression, tolerance, dependence, nausea, confusion, sedation, elevated heart rate, and post-treatment withdrawal symptoms.

Compounds of the invention may be prepared as described in the General Reaction Scheme 1 shown below:

General Scheme 1

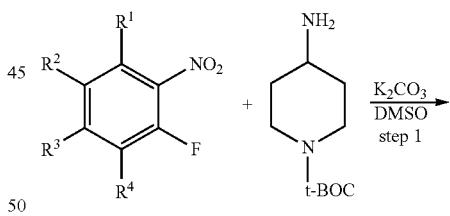

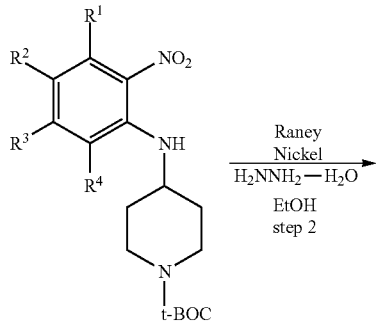

13
-continued

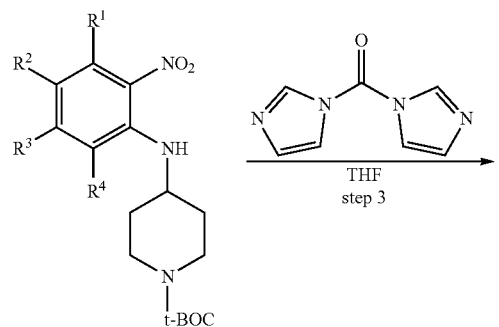

THF
step 3

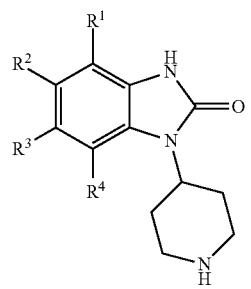

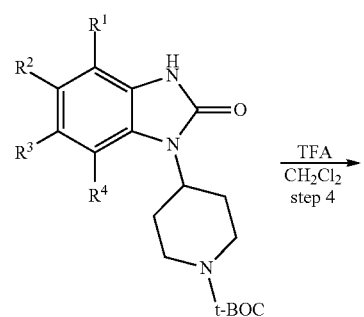

TFA
CH₂Cl₂
step 4

14
-continued

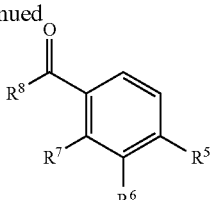

procedure A:
NaBH(OAc)₃ or
NaBH₃CN,
ClCH₂CH₂Cl for
R⁸ = H procedure B:
Ti(O/-Pr)4,
NaBH(OAc)₃ in THF or
NaBH₃CN in EtOH,
heating for
R⁸ ≠ H
step 5

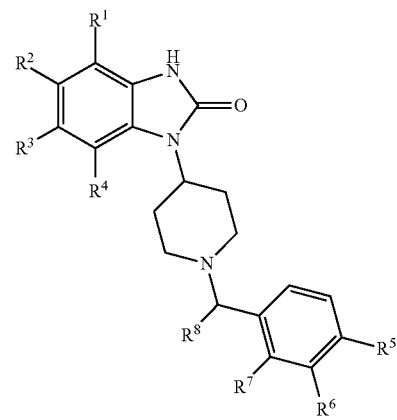

The following compounds were made according to the methods of General Scheme 1:

TABLE 1

| example | structure | R groups | step 5 reaction conditions | identification numbers |
|---|---|---|---|---|
| 1 | ![structure] | $R^2 = R^3 = Cl$, $R^5 = Br$, $R^7 = F$, other R groups = H | Procedure A, NaBH(OAc)₃ | S186 SR-14249 |
| 2 | ![structure] (±) | $R^2 = R^3 = Cl$, $R^5 = Br$, $R^8 = Me$, other R groups = H | Procedure B, Ti(Oi-Pr)₄, NaBH₃CN | S186.002 SR-14968 |

TABLE 1-continued

| example | structure | R groups | step 5 reaction conditions | identification numbers |
|---|---|---|---|---|
| 3 | 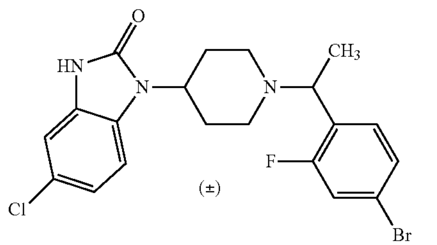 [SMILES: CC(c1ccc(Br)cc1F)N1CCC(n2c(=O)[nH]c3cc(Cl)ccc32)CC1] | $R^2$ = Cl, $R^5$ = Br, $R^7$ = F, $R^8$ = Me, other R groups = H | Procedure B, Ti(Oi-Pr)$_4$, NaBH(OAc)$_3$ | S86.025 SR-12968 |
| 4 | 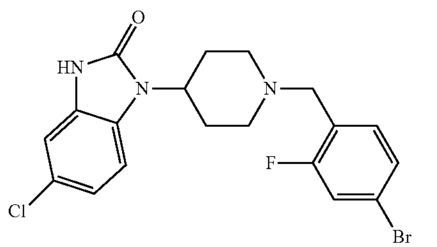 [SMILES: O=c1[nH]c2cc(Cl)ccc2n1C1CCN(Cc2ccc(Br)cc2F)CC1] | $R^2$ = Cl, $R^5$ = Br, $R^7$ = F, other R groups = H | Procedure A, NaBH(OAc)$_3$ | S86.033 SR-14152 |
| 5 | 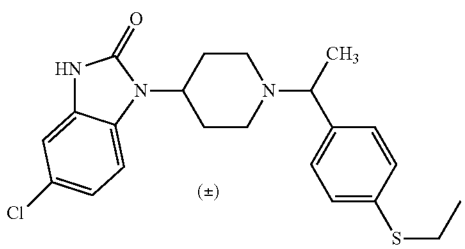 [SMILES: CCSc1ccc(C(C)N2CCC(n3c(=O)[nH]c4cc(Cl)ccc43)CC2)cc1] | $R^2$ = Cl, $R^5$ = SEt, $R^8$ = Me, other R groups = H | Procedure B, Ti(Oi-Pr)$_4$, NaBH(OAc)$_3$ | S86.014 SR-11503 |
| 6 | 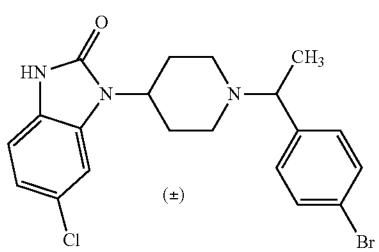 [SMILES: CC(c1ccc(Br)cc1)N1CCC(n2c(=O)[nH]c3ccc(Cl)cc32)CC1] | $R^2$ = Cl, $R^5$ = Br, $R^8$ = Me, other R groups = H | Procedure B, Ti(Oi-Pr)$_4$, NaBH(OAc)$_3$ | S112.061 SR-14167 |
| 7 | 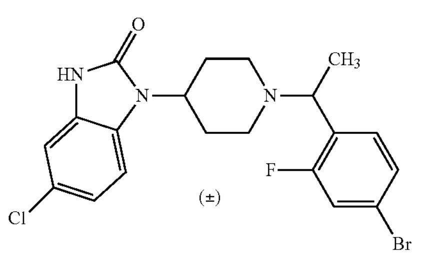 [SMILES: CC(c1ccc(Br)cc1F)N1CCC(n2c(=O)[nH]c3cc(Cl)ccc32)CC1] | $R^2$ = $R^5$ = Cl, $R^7$ = F, $R^8$ = Me, other R groups = H | Procedure B, Ti(Oi-Pr)$_4$, NaBH(OAc)$_3$ | S86.023 SR-11794 |
| 8 | 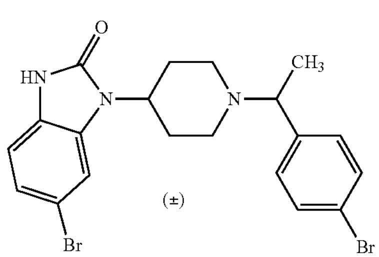 [SMILES: CC(c1ccc(Br)cc1)N1CCC(n2c(=O)[nH]c3ccc(Br)cc32)CC1] | $R^2$ = $R^5$ = Br, $R^8$ = Me, other R groups = H | Procedure B, Ti(Oi-Pr)$_4$, NaBH(OAc)$_3$ | S112.082 SR-14979 |

TABLE 1-continued

| example | structure | R groups | step 5 reaction conditions | identification numbers |
|---|---|---|---|---|
| 9 | 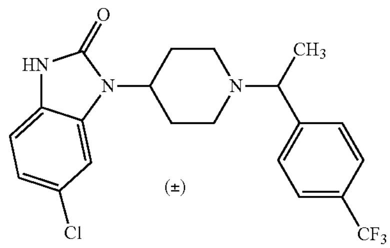 [SMILES: CC(c1ccc(C(F)(F)F)cc1)N1CCC(n2c(=O)[nH]c3ccc(Cl)cc32)CC1] | $R^3$ = Cl, $R^5$ = CF$_3$, $R^8$ = Me, other R groups = H | Procedure B, Ti(Oi-Pr)$_4$, NaBH(OAc)$_3$ | S112.064 SR-14220 |
| 10 | 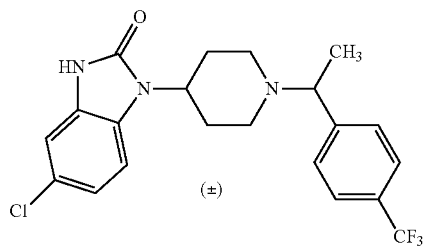 [SMILES: CC(c1ccc(C(F)(F)F)cc1)N1CCC(n2c(=O)[nH]c3cc(Cl)ccc32)CC1] | $R^2$ = Cl, $R^5$ = CF$_3$, $R^8$ = Me, other R groups = H | Procedure B, Ti(Oi-Pr)$_4$, NaBH(OAc)$_3$ | S86.037 SR-14219 |
| 11 | 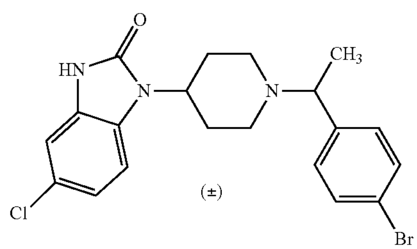 [SMILES: CC(c1ccc(Br)cc1)N1CCC(n2c(=O)[nH]c3cc(Cl)ccc32)CC1] | $R^2$ = Cl, $R^5$ = Br, $R^8$ = Me, other R groups = H | Procedure B, Ti(Oi-Pr)$_4$, NaBH(OAc)$_3$ | S86.013 SR-11502 |
| 12 | 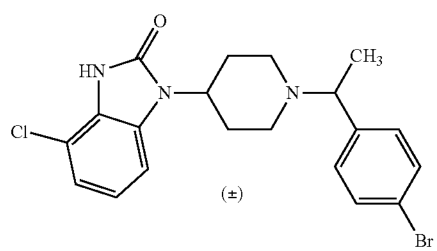 [SMILES: CC(c1ccc(Br)cc1)N1CCC(n2c(=O)[nH]c3c(Cl)cccc32)CC1] | $R^1$ = Cl, $R^5$ = Br, $R^8$ = Me, other R groups = H | Procedure B, Ti(Oi-Pr)$_4$, NaBH(OAc)$_3$ | S112.062 SR-14206 |
| 13 | 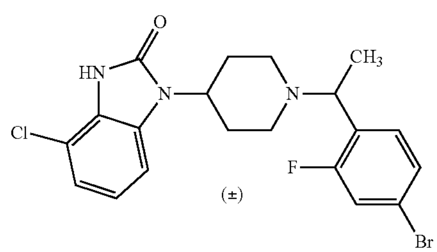 [SMILES: CC(c1ccc(Br)cc1F)N1CCC(n2c(=O)[nH]c3c(Cl)cccc32)CC1] | $R^1$ = Cl, $R^5$ = Br, $R^7$ = F, $R^8$ = Me, other R groups = H | Procedure B, Ti(Oi-Pr)$_4$, NaBH(OAc)$_3$ | S112.049 SR-13406 |
| 14 | 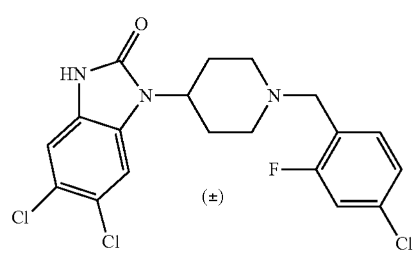 [SMILES: O=c1[nH]c2cc(Cl)c(Cl)cc2n1C1CCN(Cc2ccc(Cl)cc2F)CC1] | $R^2$ = $R^3$ = $R^5$ = Cl, $R^7$ = F, other R groups = H | Procedure A, NaBH(OAc)$_3$ | S186.004 SR-15098 |

TABLE 1-continued

| example | structure | R groups | step 5 reaction conditions | identification numbers |
|---------|-----------|----------|---------------------------|------------------------|
| 15 | 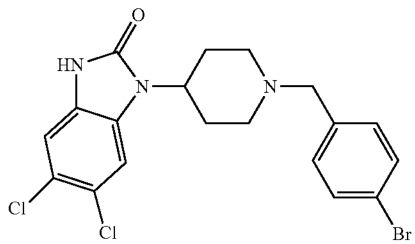 [SMILES: O=c1[nH]c2cc(Cl)c(Cl)cc2n1C1CCN(Cc2ccc(Br)cc2)CC1] | $R^2 = R^3$ = Cl, $R^5$ = Br, other R groups = H | Procedure A, NaBH(OAc)$_3$ | S186.005 SR-15099 |
| 16 | 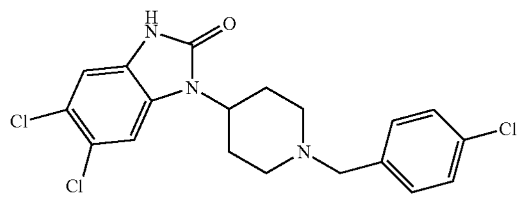 [SMILES: O=c1[nH]c2cc(Cl)c(Cl)cc2n1C1CCN(Cc2ccc(Cl)cc2)CC1] | $R^2 = R^3$ = Cl, $R^5$ = Cl, other R groups = H | Procedure A, NaBH(OAc)$_3$ | S186.006 SR-17018 |
| 17 | 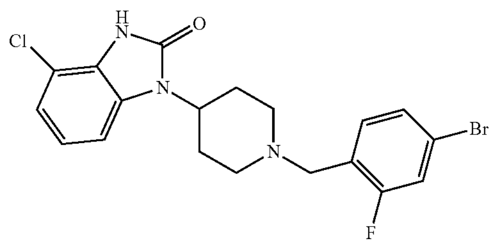 [SMILES: O=c1[nH]c2c(Cl)cccc2n1C1CCN(Cc2ccc(Br)cc2F)CC1] | $R^1$ = Cl, $R^5$ = Br, $R^7$ = F, other R groups = H | Procedure A, NaBH(OAc)$_3$ | S112.084 SR-16299 |
| 18 | 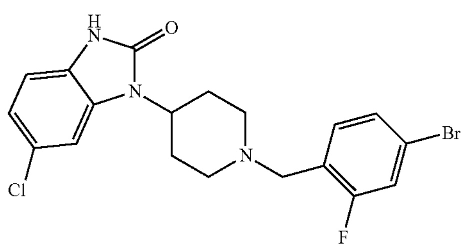 [SMILES: O=c1[nH]c2ccc(Cl)cc2n1C1CCN(Cc2ccc(Br)cc2F)CC1] | $R^3$ = Cl, $R^5$ = Br, $R^7$ = F, other R groups = H | Procedure A, NaBH(OAc)$_3$ | S112.086 SR-16301 |
| 19 | 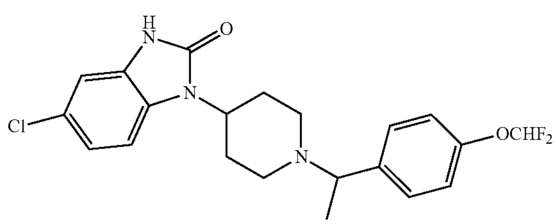 [SMILES: CC(c1ccc(OC(F)F)cc1)N1CCC(n2c(=O)[nH]c3cc(Cl)ccc32)CC1] | $R^2$ = Cl, $R^5$ = OCHF$_2$, $R^8$ = Me, other R groups = H | Procedure B, Ti(Oi-Pr)$_4$, NaBH(OAc)$_3$ | S86.026 SR-13403 |
| 20 | 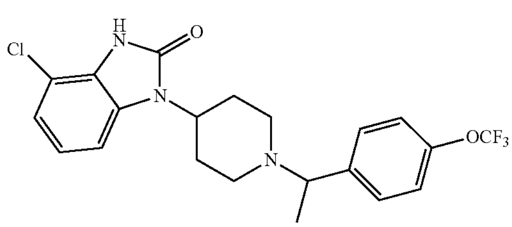 [SMILES: CC(c1ccc(OC(F)(F)F)cc1)N1CCC(n2c(=O)[nH]c3c(Cl)cccc32)CC1] | $R^1$ = Cl, $R^5$ = OCF$_3$, $R^8$ = Me, other R groups = H | Procedure B, Ti(Oi-Pr)$_4$, NaBH(OAc)$_3$ | S112.034 SR-12032 |

TABLE 1-continued

| example | structure | R groups | step 5 reaction conditions | identification numbers |
|---|---|---|---|---|
| 21 | (benzimidazol-2-one with Cl substituents, N-piperidinyl-CH(CH₃)-aryl(Cl,F)) | $R^2$ = Cl, $R^5$ = Cl, $R^7$ = F, $R^8$ = Me, other R groups = H | Procedure B, Ti(Oi-Pr)$_4$, NaBH(OAc)$_3$ | S112.041 SR-12038 |
| 22 | (Br-benzimidazol-2-one with piperidinyl-CH(CH₃)-aryl-OCF₃) | $R^3$ = Br, $R^5$ = OCF$_3$, $R^8$ = Me, other R groups = H | Procedure B, Ti(Oi-Pr)$_4$, NaBH(OAc)$_3$ | S112.076 SR-14973 |
| 23 | (Br-benzimidazol-2-one with piperidinyl-CH(CH₃)-aryl(Cl,F)) | $R^3$ = Br, $R^5$ = Cl, $R^7$ = F, $R^8$ = Me, other R groups = H | Procedure B, Ti(Oi-Pr)$_4$, NaBH(OAc)$_3$ | S112.077 SR-14974 |
| 24 | (diCl-benzimidazol-2-one with piperidinyl-CH(CH₃)-aryl-OMe) | $R^1$ = Cl, $R^3$ = Cl, $R^5$ = OMe, $R^8$ = Me, other R groups = H | Procedure B, Ti(Oi-Pr)$_4$, NaBH(OAc)$_3$ | S184 SR-12306 |
| 25 | (diCl-benzimidazol-2-one with piperidinyl-CH₂-aryl(CH₃,F)) | $R^2$ = $R^3$ = Cl, $R^5$ = Me, $R^7$ = F, other R groups = H | Procedure A, NaBH(OAc)$_3$ | S186.011 SR-18586 |

METHODS AND EXAMPLES (CHEMISTRY)

All reagents and anhydrous solvents were used as obtained from commercial vendors. $^1$H NMR spectra reported in Examples were recorded on a Brüker Ultrashield 400 at 400 MHz. Chemical shifts are reported in parts per million (ppm) using an internal standard, CHCl$_3$ (δ 7.26), MeOH (δ 3.34) or DMSO (δ 2.54). Mass spectra were recorded on a Thermo/Finnegan LCQ Duo system. Analytical HPLC spectra were obtained using an Agilent 1100 reverse phase analytical HPLC instrument, with conditions and columns as indicated. "HPLC method 1" was routinely used: column=Zorbax® 5 μm Eclipse-XDB-C18 80 Å LC column (155×4.6 mm), column temperature=40° C., flow rate=3.00 mL/min. The method incorporates a gradient elution, beginning with 98% H$_2$O/2% acetonitrile, each with 0.1% TFA. After 1 minute, hydrophobicity was increased to 5% acetonitrile and then linearly in a gradient to 95% acetonitrle over an additional 5 minutes. Detection was by UV absorbance at multiple wavelengths, typically 215, 254, and 280 nm.

Example 1

1-(1-(4-bromo-2-fluorobenzyl)piperidin-4-yl)-5,6-dichloro-1H-benzo[d]imidazol-2(3H)-one

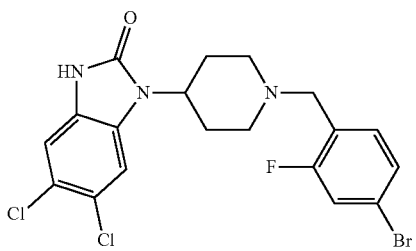 [SMILES: O=c1[nH]c2cc(Cl)c(Cl)cc2n1C1CCN(Cc2ccc(Br)cc2F)CC1]

Step 1. 1,2-Dichloro-4-fluoro-5-nitrobenzene (0.43 mL, 3.3 mmol) was added to a solution of tert-butyl 4-aminopiperidine-1-carboxylate (655 mg, 3.3 mmol) and $K_2CO_3$ (497 mg, 3.6 mmol, 1.1 equiv.) in DMSO (5 mL) and the solution was stirred at room temperature under argon overnight. Reaction progress was monitored by LCMS and upon completion, water (20 mL) was added and the organic layer extracted with ethyl acetate (3×15 mL). The combined organic layers were then washed with brine, dried over sodium sulfate, and concentrated under reduced pressure. Purification was achieved by flash column chromatography on silica gel using a gradient of ethyl acetate:hexanes as the eluent. Fractions containing the desired product were pooled and concentrated under reduced pressure to give the product as an orange solid. 788 mg of the product tert-butyl 4-((4,5-dichloro-2-nitrophenyl)amino)piperidine-1-carboxylate was obtained (62%).

Step 2. The product of step 1 (788 mg, 2.0 mmol) was dissolved in ethanol (40 mL) and a 50% aqueous suspension of Raney nickel (5 mL) was added. Hydrazine hydrate (0.98 mL, 20.0 mmol) was then added dropwise to the stirred mixture over 10 min. The mixture was heated to 45° C. and maintained at that temperature until HPLC analysis indicated that the reaction was complete (10 min). The mixture was filtered through a pad of Celite® which was washed with methanol (3×30 mL). The solvent was removed under reduced pressure. Purification was achieved by flash column chromatography on silica gel using a gradient of ethyl acetate: hexanes as the eluent Fractions containing the desired product were pooled and concentrated under reduced pressure to give the product as an gray solid. 552 mg of the product tert-butyl 4-((2-amino-4,5-dichlorophenyl)amino)piperidine-1-carboxylate was obtained (76%).

Step 3. The product of step 2 (550 mg, 1.5 mmol) was dissolved in THF (15 mL) under argon and 1,1'-carbonyldiimidazole (347 mg, 2.1 mmol) was added in one portion. The solution was stirred at room temperature overnight. Reaction progress was monitored by LCMS and upon completion the solvent was removed under reduced pressure and the residue was dissolved in ethyl acetate (20 mL). This reaction mixture was washed with 1M HCl (2×15 mL), brine (15 mL), and dried over sodium sulfate and the solvent was removed under reduced pressure. Purification was achieved by flash column chromatography on silica gel using a gradient of ethyl acetate: hexanes as the eluent. Fractions containing the desired product were pooled and concentrated under reduced pressure to give the product as a gray powder. 538 mg of the product tert-butyl 4-(5,6-dichloro-2-oxo-2,3-dihydro-1H-benzo[d]imidazol-1-yl)piperidine-1-carboxylate was obtained (91%).

Step 4. The product of step 3 (538 mg, 1.4 mmol) was dissolved in a 33% solution of trifluoroacetic acid in dichloromethane (4 mL). Reaction progress was monitored by LCMS and after 2 hours the solvent was removed under reduced pressure and the residue was dissolved in a minimal amount of water-acetonitrile (1:1). The solution was frozen and then was subjected to lyophilization overnight, giving the product as a grey solid, in the form of a trifluoroacetic acid salt. This material was taken to step 5 without further purification, obtained in 86% crude yield.

Step 5. $NaBH(OAc)_3$ (169 mg, 0.81 mmol) was added to an anhydrous dichloroethane (3 mL) solution of the product of step 4, 5,6-dichloro-1-(piperidin-4-yl)-1H-benzo[d]imidazol-2(3H)-one (102 mg, 0.27 mmol), and 4-bromo-2-fluorobenzaldehyde (162 mg, 0.81 mmol). The mixture was stirred at room temperature under argon. A few drops of acetic acid were added to the solution, which was then stirred overnight under argon. Reaction progress was monitored by LCMS and when complete, saturated sodium bicarbonate (5 mL) was added to the reaction mixture, which was then diluted with dichloromethane (10 mL). The aqueous layer was extracted with dichloromethane (2×10 mL). The combined organic layers were washed with brine (10 mL), dried over sodium sulfate, and concentrated under reduced pressure. Purification was achieved by flash column chromatography on silica gel using dichloromethane:methanol as the eluent. Fractions containing the desired product were pooled and concentrated under reduced pressure to give the product as a clear residue. This residue was dissolved in a minimal amount of water-acetonitrile (1:1). The solution was frozen and subjected to lyophilization overnight, giving the product as a white powder. 48.1 mg of the product 1-(1-(4-bromo-2-fluorobenzyl)piperidin-4-yl)-5,6-dichloro-1H-benzo[d]imidazol-2(3H)-one was obtained (38%).

Acids (e.g., HCl, $MeSO_3H$, $CF_3CO_2H$, etc.) could be added to the product before the lyophilization step to give the corresponding addition salts of the product. As one example, the mesylate salt was obtained as follows: Methanesulfonic acid (13.1 µL, 0.20 mmol) was added to a suspension of 1-(1-(4-bromo-2-fluorobenzyl)piperidin-4-yl)-5,6-dichloro-1H-benzo[d]imidazol-2(3H)-one (prepared as described above, following the flash chromatography element of step 5, 95.9 mg, 0.20 mmol) in ethanol (2 mL). The mixture was heated to 60° C. for 30 min. The solvent was evaporated under reduced pressure to give the product as a clear residue. This residue was dissolved in a minimal amount of water-acetonitrile (1:1). The solution was frozen and subjected to lyophilization overnight, giving 1-(1-(4-bromo-2-fluorobenzyl)piperidin-4-yl)-5,6-dichloro-1H-benzo[d]imidazol-2(3H)-one methanesulfonate as an white powder (92.3 mg, 85% yield).

Supporting data for the product of Example 1: $^1H$ NMR of the mesylate salt (400 MHz, MeOD) δ 7.64-7.55 (m, 3H), 7.47 (s, 1H), 7.20 (s, 1H), 4.53 (tt, J=18.58, 4.23, 1H), 4.45 (s, 2H), 3.70 (d, J=12.68, 2H), 3.37-3.26 (m, 2H), 2.83-2.69 (m, 5H), 2.09 (d, J=14.88, 2H). MS(m/z): [M+H] calc'd for $C_{19}H_{17}BrCl_2FN_3O$ 472.00 and 474.00, found 472.31 and 474.18. HPLC $t_R$=4.00 min (HPLC method 1); purity=95.4%. $^1H$ NMR of the free base form (400 MHz, $CDCl_3$) δ 8.94 (s, 1H), 7.36-7.22 (m, 4H), 7.16 (s, 1H), 4.25 (tt, J=18.79, 4.30, 1H), 3.60 (s, 2H), 3.04 (d, J=11.44, 2H), 2.38 (qd, J=12.39, 3.45, 2H), 2.22 (t. J=11.08, 2H), 1.80 (dd, J=11.82, 2.41, 2H).

Example 2

1-(1-(1-(4-bromophenyl)ethyl)piperidin-4-yl)-5,6-dichloro-1H-benzo[d]imidazol-2(3H)-one

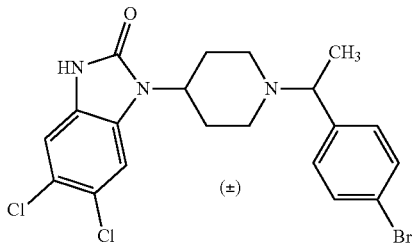 [SMILES: CC(c1ccc(Br)cc1)N1CCC(n2c(=O)[nH]c3cc(Cl)c(Cl)cc32)CC1]

(±)

This compound was made according to the method of Example 1, with the alteration in step 5 of using procedure B, including titanium (IV) isopropoxide added prior to the addition of the reducing agent, which was in this case NaBH$_3$CN. Procedure B was always used when a substituted acetophenone compound was used as the carbonyl group-containing reactant in step 5.

Steps 1-4: Repeat of steps 1-4 in Example 1.

Step 5. Ti(Oi-Pr)$_4$ (0.5 mL, 1.6 mmol) was added to the product of step 4, 5,6-dichloro-1-(piperidin-4-yl)-1H-benzo[d]imidazol-2(3H)-one (67.2 mg, 0.16 mmol), and 1-(4-bromophenyl)ethanone (100.0 mg, 0.5 mmol) under argon. The reaction mixture was heated to 60° C. for 2 hours. The solution was then cooled to room temperature and ethanol (2 mL) was added followed by NaCNBH$_3$ (86.4 mg, 1.4 mmol) and mixture was stirred overnight under argon. The reaction progress was monitored by LCMS and upon completion saturated sodium bicarbonate (10 mL) was added. The quenched reaction was then filtered through a pad of Celite® and washed with dichloromethane (3×10 mL) and methanol (2×10 mL). The solvents were removed under reduced pressure and then the residue was dissolved in dichloromethane. This solution was washed with water. The aqueous layer was extracted with dichloromethane (3×10 mL). The combined organic layers were washed with brine (10 mL), dried over sodium sulfate, and concentrated under reduced pressure. Purification was achieved using preparative HPLC column chromatography and 0.1% TFA in H$_2$O:methanol:acetonitrile as the eluent. Fractions containing the desired product were pooled and concentrated under reduced pressure to give the product as a colorless solid, as the trifluoroacetic acid salt. This residue was dissolved in a minimal amount of water-acetonitrile (1:1). The solution was frozen and subjected to lyophilization overnight, giving the product as a white solid, in the form of a trifluoroacetic acid salt. 27.2 mg of the product 1-(1-(1-(4-bromophenyl)ethyl)piperidin-4-yl)-5,6-dichloro-1H-benzo[d]imidazol-2(3H)-one (trifluoroacetic acid salt) was obtained (28%).

Other acid addition salts (e.g., HCl, MeSO$_3$H, etc.) can be obtained instead of the trifluoroacetic acid salts by neutralization to the free base form followed by acid addition and isolation as shown for the mesylate salt in Example 1.

Supporting data for the product of Example 2 includes: $^1$H NMR (400 MHz, CDCl$_3$) δ 9.06 (s, 1H), 7.47 (d, J=8.40, 2H), 7.31 (s, 1H), 7.24 (d, J=8.48, 2H), 7.16 (s, 1H), 4.19 (tt, J=18.93, 4.27, 1H), 3.47 (q, J=6.70, 1H), 3.19 (d, J=10.40, 1H), 2.95 (d, J=9.88, 1H), 2.44-2.22 (m, 2H), 2.13 (td, J=17.63, 2.19, 1H), 2.02 (td, J=17.78, 2.23, 1H), 1.82 (d, J=13.00, 1H), 1.72 (d, J=12.17, 1H), 1.38 (d, J=6.72, 3H), MS(m/z): [M+H] calc'd for C$_{20}$H$_{20}$BrCl$_2$N$_3$O, 468.0 and 470.0; found, 468.8 and 470.2. HPLC t$_R$=4.01 min (HPLC method 1); purity=98.7%.

Anticipated procedural variations for Examples 1-2: The reagents used in these Examples are fully suited for the indicated syntheses but an experimentalist is not limited to the described reagents and/or reaction conditions, as one of ordinary skill may recognize other suitable reagents and/or reaction conditions. Specific common variants are here specified: While tert-butyl 4-aminopiperidine-1-carboxylate was used as the starting material, other N$^1$-protecting groups on the 4-aminopiperidine reactant can instead be used, with a corresponding adjustment in how step 4 (protecting group removal) is conducted. Bases and solvents other than the indicated K$_2$CO$_3$ in DMSO method are suitable for use in step 1. Reducing conditions other than the indicated combination of Raney nickel and hydrazine in ethanol can be used for nitro group reduction in step 2. Reagents other than carbonyl diimidazole can be used in step 3 to form the benzimidazolone ring, including triphosgene or a phosgene solution, as examples. Other reaction conditions and/or reducing agents may be used in step 5 to form the indicated products. The purification protocols, by flash chromatography or by preparative HPLC, may be used interchangeably in either example. Other purification methods may alternatively be used (e.g., recrystallization).

Example 3

1-(1-(1-(4-bromo-2-fluorophenyl)ethyl)piperidin-4-yl)-5-chloro-1H-benzo[d]imidazol-2(3H)-one

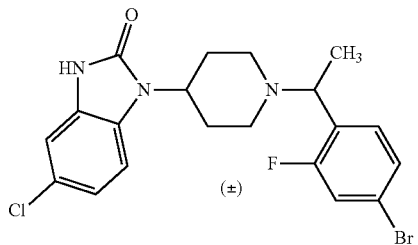 [SMILES: CC(c1ccc(Br)cc1F)N1CCC(n2c(=O)[nH]c3cc(Cl)ccc32)CC1]

(±)

This compound was made according to the method of Example 2, following General Scheme 1 but beginning with the commercially available starting material 5-chloro-1-(piperidin-4-yl)-1H-benzo[d]imidazol-2(3H)-one (obtained from Acros Organics). This material corresponds to the product of step 4 in General Scheme 1. It was converted to the product using 1-(4-bromo-2-fluorophenyl)ethanone, Ti(OiPr)$_4$, NaBH(OAc)$_3$s and THF in step 5, as generally described in Example 2, with purification by flash chromatography. The yield for the final step was 56%.

Supporting data for the product of Example 3 includes: $^1$H NMR (400 MHz, CDCl$_3$) δ 8.53 (s, 1H), 7.31-7.19 (m, 2H), 7.15 (d, J=9.36, 1H), 7.08 (d, J=8.40, 1H), 6.98-6.92 (m, 2H), 4.13-4.18 (m, 1H), 3.83 (q, J=12.96, 6.83, 1H), 3.15 (d, J=12.96, 1H), 2.89 (d, J=10.48, 1H), 2.29 (dq, J=12.32, 4.28, 1H), 2.42-2.19 (m, 1H), 2.09-1.86 (m, 2H), 1.75 (d, J=12.44, 1H), 1.65 (d, J=11.16, 1H), 1.31 (d, J=6.72, 3H), MS(m/z): [M+H] calc'd for C$_{20}$H$_{20}$BrClFN$_3$O, 452.0 and 454.0; found, 452.6 and 454.0. HPLC t$_R$=5.02 min (HPLC method 1); purity=99.0%.

Example 4

1-(1-(4-bromo-2-fluorobenzyl)piperidin-4-yl)-5-chloro-1H-benzo[d]imidazol-2(3H)-one

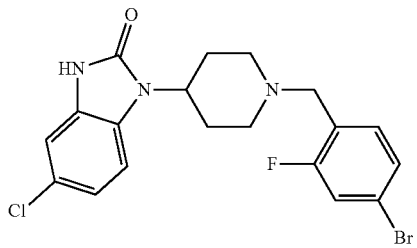 [SMILES: O=c1[nH]c2cc(Cl)ccc2n1C1CCN(Cc2ccc(Br)cc2F)CC1]

This compound was made according to the method of Example 3, using 1-(4-bromo-2-fluorophenyl)ethanone in the final step. The yield was 63%.

Supporting data for the product of Example 4 includes: $^1$H NMR (400 MHz, CDCl$_3$) δ 10.12 (s, 1H), 7.37-7.22 (m, 3H), 7.16 (d, J=8.16, 1H), 7.12 (d, J=1.96, 1H), 7.02 (dd, J=8.48, 2.00, 1H), 4.31 (tt, J=12.41, 4.23, 1H), 3.60 (s, 2H), 3.04 (d, J=11.40, 2H), 2.49-2.35 (m, 2H), 2.24 (t, J=11.28, 2H), 1.80 (dd, J=11.94, 2.02, 2H), MS(m/z): [M+H] calc'd for C$_{19}$H$_{18}$BrClFN$_3$O, 438.03 and 440.03; found, 438.63 and 440.11. HPLC t$_R$=3.66 min (HPLC method 1); purity=95.3%.

Example 5

5-chloro-1-(1-(1-(4-(ethylthio)phenyl)ethyl)piperidin-4-yl)-1H-benzo[d]imidazol-2(3H)-one

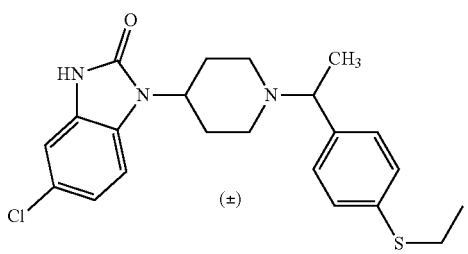 [SMILES: CCSc1ccc(C(C)N2CCC(n3c(=O)[nH]c4cc(Cl)ccc43)CC2)cc1]

This compound was made according to the method of Example 3, using 1-(4-(ethylthio)phenyl)ethanone. Ti(OiPr)$_4$ and NaBH(OAc)$_3$ in the final step. The yield was 45%.

Supporting data for the product of Example 5 includes: $^1$H NMR (400 MHz, CDCl$_3$) δ 10.08 (s, 1H), 7.23-7.17 (m, 4H), 7.09 (d, J=8.48, 1H), 7.03 (d, J=2.00, 1H), 6.94 (dd, J=8.48, 2.04, 1H), 4.18 (tt, J=16.69, 4.24, 1H), 3.43 (q, J=13.40, 6.64, 1H), 3.10 (d, J=11.44, 1H), 2.89-2.84 (m, 3H), 2.35 (dq, J=12.28, 4.04, 1H), 2.24 (dq, J=12.36, 3.91, 1H), 2.08 (dt, J=11.60, 2.16, 1H), 1.96 (dt, J=11.72, 2.12, 1H) 1.73 (dd, J=10.64, 2.02, 1H), 1.65-1.63 (m, 1H), 1.30 (d, J=6.93, 3H), 1.25 (t, J=8.01, 3H), MS(m/z): [M+H] calc'd for C$_{22}$H$_{26}$ClN$_3$OS, 416.1; found, 416.1. HPLC t$_R$=3.97 min (HPLC method 1); purity=99.9%.

Example 6

1-(1-(1-(4-bromophenyl)ethyl)piperidin-4-yl)-6-chloro-1H-benzo[d]imidazol-2(3H)-one

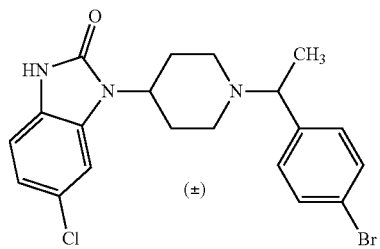 [SMILES: CC(c1ccc(Br)cc1)N1CCC(n2c(=O)[nH]c3ccc(Cl)cc32)CC1]

This compound was made according to the method of Example 2, using 5-chloro-1-fluoro-2-nitrobenzene in step 1 and 1-(4-bromophenyl)ethanone, Ti(OiPr)$_4$ and NaBH(OAc)$_3$ in the final step. The overall yield was 20%.

Supporting data for the product of Example 6 includes: $^1$H NMR (400 MHz, CDCl$_3$) δ 9.83 (s, 1H), 7.40 (d, J=7.47, 2H), 7.17-6.92 (m, 5H), 4.29-4.09 (m, 1H), 3.39 (d, J=5.52, 1H), 3.12 (d, J=9.04, 1H), 2.87 (d, J=8.52, 1H), 2.36-2.24 (m, 2H), 1.94-2.11 (m, 2H) 1.77-1.61 (m, 2H), 1.31 (d, J=5.20, 3H), MS(m/z): [M+H] calc'd for C$_{20}$H$_{21}$BrClN$_3$O, 434.0 and 436.0; found, 434.0 and 436.0. HPLC t$_R$=4.07 min (HPLC method 1); purity=99.0%.

Example 7

5-chloro-1-(1-(1-(4-chloro-2-fluorophenyl)ethyl)piperidin-4-yl)-1H-benzo[d]imidazol-2(3H)-one

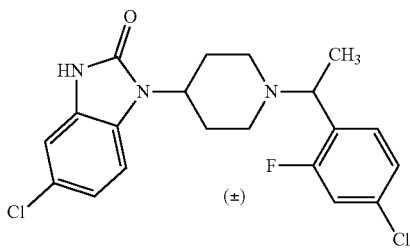 [SMILES: CC(c1ccc(Cl)cc1F)N1CCC(n2c(=O)[nH]c3cc(Cl)ccc32)CC1]

This compound was made according to the method of Example 3, using 1-(4-chloro-2-fluorophenyl)ethanone, Ti(Oi-Pr)$_4$ and NaBH(OAc)$_3$ in the final step, following the general protocol of Example 2. The overall yield was 31%.

Supporting data for the product of Example 7 includes: $^1$H NMR (400 MHz, CDCl$_3$) δ 8.98 (s, 1H), 7.32 (t. J=16.09, 8.08, 1H), 7.09-6.99 (m, 4H), 6.96 (dd, J=10.44, 2.00, 1H), 4.16 (tt, J=12.48, 4.24, 1H), 3.85 (q, J=13.64, 6.76, 1H), 3.16 (d, J=11.56, 1H), 2.90 (d, J=11.24, 1H), 2.36 (dq, J=12.36, 4.12, 1H), 2.24 (dq, J=12.40, 3.92, 1H), 2.12-2.07 (m, 1H), 1.93 (dt, J=11.56, 1.80, 1H) 1.67-1.60 (m, 2H), 1.32 (d, J=6.80, 3H), MS(m/z): [M+H] calc'd for C$_{20}$H$_{20}$Cl$_2$FN$_3$O, 408.1; found, 408.4. HPLC t$_R$=3.73 min (HPLC method 1); purity=99.8%.

Example 8

6-bromo-1-(1-(1-(4-bromophenyl)ethyl)piperidin-4-yl)-1H-benzo[d]imidazol-2(3H)-one

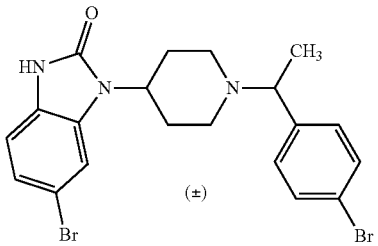 [SMILES: CC(c1ccc(Br)cc1)N1CCC(n2c(=O)[nH]c3ccc(Br)cc32)CC1]

This compound was made according to the method of Example 2, using 4-bromo-2-fluoro-1-nitrobenzene in step 1 and 1-(4-bromophenyl)ethanone. Ti(Oi-Pr)$_4$ and NaBH(OAc)$_3$ in the final step. The overall yield was 5%.

Supporting data for the product of Example 8 includes: $^1$H NMR (400 MHz, CDCl$_3$) δ 8.77 (s, 1H), 7.46 (d, J=8.36, 2H), 7.31 (d, J=1.08, 1H), 7.20-7.15 (m, 2H), 7.10 (dd, J=8.32, 1.77, 1H), 6.86 (d, J=6.32, 1H), 4.13 (tt, J=12.48, 4.08, 1H), 3.41 (q, J=13.32, 6.60, 1H), 3.13 (d, J=10.64, 1H), 2.87 (d, J=10.32, 1H), 2.29 (dq, J=12.32, 4.28, 1H), 2.24 (dq, J=12.16, 3.96, 1H), 2.10-2.05 (m, 1H), 1.98 (dt, J=11.96, 2.00, 1H) 1.75 (d, J=12.40, 1H), 1.64 (d, J=12.12, 1H), 1.31 (d, J=6.72, 3H). MS(m/z): [M+H] calc'd for C$_{20}$H$_{21}$Br$_2$N$_3$O, 480.1: found. 480.2. HPLC t$_R$=3.93 min (HPLC method 1); purity=99.8%.

Example 9

6-chloro-1-(1-(1-(4-(trifluoromethyl)phenyl)ethyl)piperidin-4-yl)-1H-benzo[d]imidazol-2(3H)—

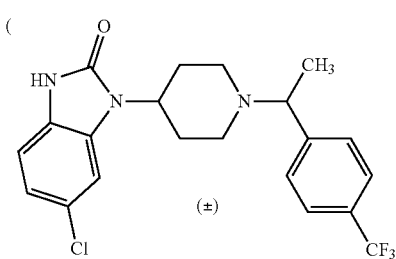 [SMILES: CC(c1ccc(C(F)(F)F)cc1)N1CCC(n2c(=O)[nH]c3ccc(Cl)cc32)CC1]

This compound was made according to the method of Example 6, using 1-(4-(trifluoromethyl)phenyl)ethanone in step 5. The overall yield was 17%.

Supporting data for the product of Example 9 includes: $^1$H NMR (400 MHz, MeOD) δ 7.56 (d, J=8.20, 2H), 7.48 (d, J=8.21, 2H), 7.37 (d, J=1.64, 1H), 6.94 (dd, J=8.32, 1.80, 1H), 6.89 (d J=8.32, 1H), 4.09 (tt, J=12.52, 4.40, 1H), 3.40 (q, J=8.00, 1H), 3.22-3.20 (m, 1H), 2.91-2.86 (m, 1H), 2.35 (dq, J=12.28, 4.04, 1H), 2.42 (dq, J=12.52, 4.72, 1H), 2.10 (dt, J=11.92, 2.56, 1H), 1.99 (dt, J=12.00, 2.44, 1H) 1.72-1.56 (m, 2H), 1.37 (d, J=6.76, 3H), MS(m/z): [M+H] calc'd for C$_{21}$H$_{21}$ClF$_3$N$_3$O, 424.1; found, 424.4. HPLC t$_R$=5.23 min (HPLC method 1); purity=96.1%.

Example 10

5-chloro-1-(1-(1-(4-(trifluoromethyl)phenyl)ethyl)piperidin-4-yl)-1H-benzo[d]imidazol-2(3H)-one

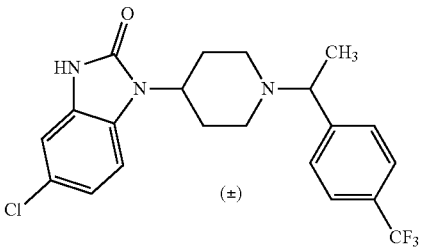 [SMILES: CC(c1ccc(C(F)(F)F)cc1)N1CCC(n2c(=O)[nH]c3cc(Cl)ccc32)CC1]

This compound was made according to the method of Example 3, using 1-(4-(trifluoromethyl) phenyl)ethanone, Ti(OiPr)$_4$ and NaBH(OAc)$_3$ in the final step. The overall yield was 21%.

Supporting data for the product of Example 10 includes: $^1$H NMR (400 MHz, MeOD) δ 7.56 (d, J=8.20, 2H), 7.48 (d, J=8.24, 2H), 7.22 (d, J=9.04, 1H), 6.98-6.94 (m, 2H), 4.09 (tt, J=12.44, 4.36, 1H), 3.39 (q, J=13.56, 6.80, 1H), 3.21-3.17 (m, 1H), 2.89-2.82 (m, 1H), 2.44 (dq, J=12.40, 4.12, 1H), 2.30 (dq, J=12.48, 4.04, 1H), 2.10 (dt, J=11.92, 2.56, 1H), 1.98 (dt, J=12.00, 2.36, 1H) 1.70-1.58 (m, 2H), 1.36 (d, J=6.76, 3H), MS(m/z): [M+H] calc'd for C$_{21}$H$_{21}$ClF$_3$N$_3$O, 424.1; found, 424.3. HPLC t$_R$=5.17 min (HPLC method 1); purity=95.0%.

Example 11

1-(1-(1-(4-bromophenyl)ethyl)piperidin-4-yl)-5-chloro-1H-benzo[d]imidazol-2(3H)-one

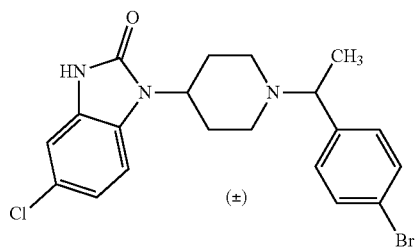 [SMILES: CC(c1ccc(Br)cc1)N1CCC(n2c(=O)[nH]c3cc(Cl)ccc32)CC1]

This compound was made according to the method of Example 3, using 1-(4-bromophenyl)ethanone, Ti(OiPr)$_4$ and NaBH(OAc)$_3$ in the final step. The overall yield was 19%.

Supporting data for the product of Example 11 includes: $^1$H NMR (400 MHz, CDCl$_3$) δ 9.01 (s, 1H), 7.37 (d, J=8.36, 2H), 7.16 (d, J=8.36, 2H), 7.08 (d, J=18.48, 1H), 6.99 (d, J=1.92, 1H), 6.95 (dd, J=8.40, 1.92, 1H), 4.15 (tt, J=12.32, 3.92, 1H), 3.38 (q, J=13.20, 6.56, 1H), 3.10 (d, J=10.68, 1H), 2.85 (d, J=9.72, 1H), 2.32 (dq, J=12.44, 4.12, 1H), 2.23 (dq, J=12.20, 3.88, 1H), 2.09-1.94 (m, 2H) 1.74 (d, J=10.80, 1H), 1.64 (d, J=11.28, 1H), 1.28 (d, J=6.72, 3H), MS(m/z): [M+H] calc'd for C$_{20}$H$_{21}$BrClN$_3$O, 434.1 and 436.1; found, 434.1 and 436.1. HPLC t$_R$=3.82 min (HPLC method 1); purity=99.9%.

Example 12

1-(1-(1-(4-bromophenyl)ethyl)piperidin-4-yl)-4-chloro-1H-benzo[d]imidazol-2(3H)-one

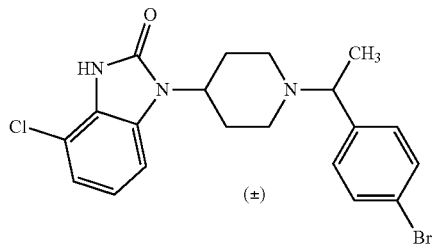 [SMILES: CC(c1ccc(Br)cc1)N1CCC(n2c(=O)[nH]c3c(Cl)cccc32)CC1]

This compound was made according to the method of Example 2, using 1-chloro-3-fluoro-2-nitrobenzene in step 1 and 1-(4-bromophenyl)ethanone, Ti(OiPr)$_4$ and NaBH(OAc)$_3$ in the final step. The overall yield was 14%.

Supporting data for the product of Example 12 includes: $^1$H NMR (400 MHz, CDCl$_3$) δ 8.63 (s, 1H), 7.49 (d, J=8.48, 2H), 7.28-7.26 (m, 3H), 7.05 (dd, J=8.32, 1.84, 1H), 6.98 (d, J=8.28, 1H), 4.25 (tt, J=12.56, 4.32, 1H), 3.48 (q, J=13.36, 6.64, 1H), 3.21 (d, J=9.96, 1H), 2.98-2.94 (m, 1H), 2.43 (dq, J=12.76, 4.24, 1H), 2.33 (dq, J=12.36, 4.08, 1H), 2.17 (dt, J=11.72, 2.40, 1H), 2.06 (dt, J=11.72, 2.24, 1H), 1.86-1.73 (m, 2H), 1.40 (d, J=6.72, 3H), MS(m/z): [M+H] calc'd for C$_{20}$H$_{21}$BrClN$_3$O, 434.1 and 436.1; found, 434.1 and 436.1. HPLC t$_R$=3.88 min (HPLC method 1); purity=99.9%.

Example 13

1-(1-(1-(4-bromo-2-fluorophenyl)ethyl)piperidin-4-yl)-4-chloro-1H-benzo[d]imidazol-2(3H)—

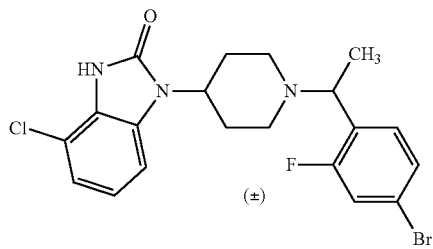 [SMILES: CC(c1ccc(Br)cc1F)N1CCC(n2c(=O)[nH]c3c(Cl)cccc32)CC1]

This compound was made according to the method of Example 12, using 1-(4-bromo-2-fluorophenyl)ethanone in the final step. The overall yield was 13%.

Supporting data for the product of Example 13 includes: $^1$H NMR (400 MHz, CDCl$_3$) δ 9.09 (s, 1H), 7.37-7.15 (m, 4H), 6.96 (dd, J=8.32, 1.84, 1H), 6.90 (d, J=8.32, 1H), 4.14 dt, J=12.56, 4.12, 1H), 3.85 (q, J=13.60, 6.76, 1H), 3.19 (d, J=10.76, 1H), 2.87 (dd, J=29.44, 9.32, 1H), 2.36 (dq, J=12.32, 4.08, 1H), 2.24 (dq, J=12.24, 4.24, 1H), 2.15-1.90 (m, 2H), 1.78-1.64 (m, 2H), 1.33 (d, J=6.80, 3H), MS(m/z): [M+H] calc'd for C$_{20}$H$_{20}$BrClFN$_3$O, 454.0 and 452.1; found, 454.0 and 452.1. HPLC t$_R$=5.09 min (HPLC method 1); purity=99.0%.

Example 14

5,6-dichloro-1-(1-(4-chloro-2-fluorobenzyl)piperidin-4-yl)-1H-benzo[d]imidazol-2(3H)-one

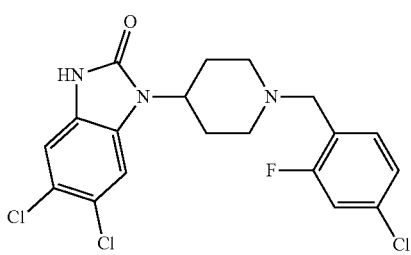 [SMILES: O=c1[nH]c2cc(Cl)c(Cl)cc2n1C1CCN(Cc2ccc(Cl)cc2F)CC1]

This compound was made according to the method of Example 1, using 4-chloro-2-fluorobenzaldehyde in step 5. The overall yield was 49%.

Supporting data for the product of Example 14 includes: $^1$H NMR (400 MHz, CDCl$_3$) δ 9.09 (s, 1H), 7.39 (t, J=8.06, 1H), 7.31 (s, 1H), 7.18-7.13 (m, 2H), 7.10 (dd, J=9.56, 1.84, 1H), 4.32-4.20 (m, 1H), 3.62 (s, 2H), 3.05 (d, J=11.53, 2H), 2.46-2.31 (m, 2H), 2.23 (t, J=11.56, 2H), 1.80 (d, J=10.20, 2H), MS(m/z): [M+H] calc'd for C$_{19}$H$_{17}$Cl$_3$FN$_3$O, 428.0 and 430.0; found. 428.3 and 430.2. HPLC t$_R$=3.95 min (HPLC method 1); purity=96.3%.

Example 15

1-(1-(4-bromobenzyl)piperidin-4-yl)-5,6-dichloro-1H-benzo[d]imidazol-2(3H)-one

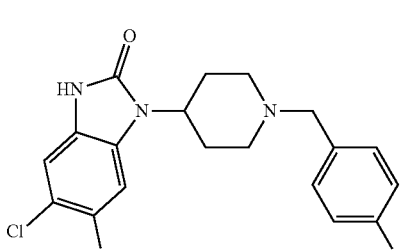

This compound was made according to the method of Example 1, using 4-bromobenzaldehyde in step 5. The overall yield was 55%.

Supporting data for the product of Example 15 includes: $^1$H NMR (400 MHz, CDCl$_3$) δ 8.68 (s, 1H), 7.47 (d, J=7.88, 2H), 7.32 (s, 1H), 7.29-7.22 (m, 2H), 7.15 (s, 1H), 4.35-4.23 (m, 1H), 3.52 (s, 2H), 3.02 (d, J=11.44, 2H), 2.44-2.29 (m, 2H), 2.15 (t, J=11.58, 2H), 1.78 (d, J=10.60, 2H), MS(m/z): [M+H] calc'd for C$_{19}$H$_{18}$BrCl$_2$N$_3$O, 454.00 and 456.00; found, 454.32 and 456.22. HPLC to =3.99 min (HPLC method 1); purity=95.9%.

Example 16

1-(1-(4-chlorobenzyl)piperidin-4-yl)-5,6-dichloro-1H-benzo[d]imidazol-2(3H)-one

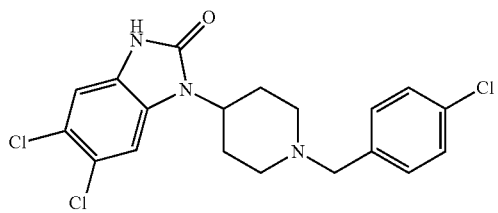 [SMILES: O=c1[nH]c2cc(Cl)c(Cl)cc2n1C1CCN(Cc2ccc(Cl)cc2)CC1]

This compound was made according to the method of Example 1, using 4-chlorobenzaldehyde in step 5. The overall yield was 46%.

Supporting data for the product of Example 16 includes: $^1$H NMR (400 MHz, Methanol-$d_4$) δ 7.60-7.52 (m, 4H), 7.49 (s, 1H), 7.19 (s, 1H), 4.53 (tt, J=12.3, 4.2 Hz, 1H), 4.39 (s, 2H), 3.65 (d, J=12.0 Hz, 2H), 3.30-3.20 (m, 2H), 2.73 (s, 5H), 2.08 (d, J=14.0 Hz, 2H); MS(m/z): [M+H] calc'd for $C_{19}H_{19}Cl_3N_3O$, 410.1; found, 410.1.

Example 17

1-(1-(4-bromo-2-fluorobenzyl)piperidin-4-yl)-4-chloro-1H-benzo[d]imidazol-2(3H)-one

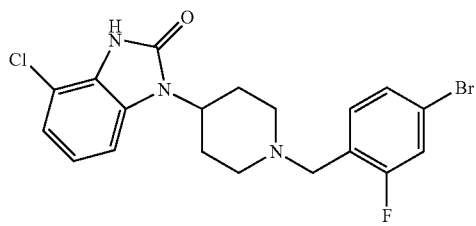 [SMILES: O=c1[nH]c2c(Cl)cccc2n1C1CCN(Cc2ccc(Br)cc2F)CC1]

This compound was made according to the method of Example 12, using 2-fluoro-4-bromobenzaldehyde in step 5. The overall yield was 39%.

Supporting data for the product of Example 17 includes: $^1$H NMR (400 MHz, Methanol-$d_4$) δ 7.65-7.55 (m, 3H), 7.20 (dd, J=5.9, 3.0 Hz, 1H), 7.13-7.05 (m, 2H), 4.54 (ddt, J=12.3, 8.2, 4.1 Hz, 1H), 4.45 (s, 2H), 3.71 (d, J=12.5 Hz, 2H), 3.36-3.30 (m, 2H), 2.80 (qd, J=13.5, 3.9 Hz, 2H), 2.71 (s, 3H), 2.10 (d, J=14.1 Hz, 2H); MS(m/z): [M+H] calc'd for $C_{19}H_{19}BrClFN_3O$, 440.0 and 438.0; found, 440.0 and 438.0.

Example 18

1-(1-(4-bromo-2-fluorobenzyl)piperidin-4-yl)-6-chloro-1H-benzo[d]imidazol-2(3H)-one

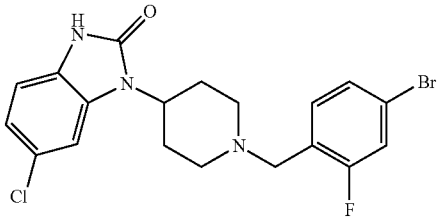 [SMILES: O=c1[nH]c2ccc(Cl)cc2n1C1CCN(Cc2ccc(Br)cc2F)CC1]

This compound was made according to the method of Example 6, using 2-fluoro-4-bromobenzaldehyde in the final step. The overall yield was 31%.

Supporting data for the product of Example 18 includes: $^1$H NMR (400 MHz, Methanol-$d_4$) δ 7.64-7.54 (m, 3H). 7.36 (dd, J=1.9, 0.5 Hz, 1H), 7.11-6.99 (m, 2H), 4.55 (tt, J=12.3, 4.3 Hz, 1H), 4.45 (d, J=1.3 Hz, 2H), 3.70 (d. J=12.3 Hz, 2H), 3.36-3.30 (m, 2H). 2.83-2.72 (m, 5H), 2.09 (d, J=14.2 Hz, 2H); MS(m/z): [M+H] calc'd for $C_{19}H_{19}BrClFN_3O$, 440.0 and 438.0; found, 440.0 and 438.0.

Example 19

5-chloro-1-(1-(1-(4-(difluoromethoxy)phenyl)ethyl)piperidin-4-yl)-1H-benzo[d]imidazol-2(3H)-one

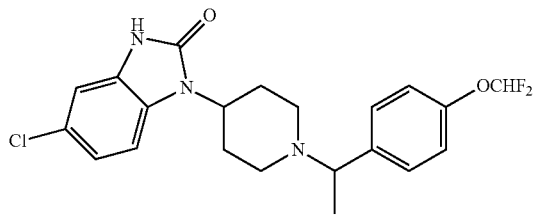 [SMILES: CC(c1ccc(OC(F)F)cc1)N1CCC(n2c(=O)[nH]c3cc(Cl)ccc32)CC1]

This compound was made according to the method of Example 5, using 1-(4-(difluoromethoxy)phenyl)ethanone in the final step. The overall yield was 35%.

Supporting data for the product of Example 19 includes: MS(m/z): [M+H] calc'd for $C_{21}H_{23}ClF_2N_3O_2$, 422.1; found, 422.2.

Example 20

4-chloro-1-(1-(1-(4-(trifluoromethoxy)phenyl)ethyl)piperidin-4-yl)-1H-benzo[d]imidazol-2(3H)-one

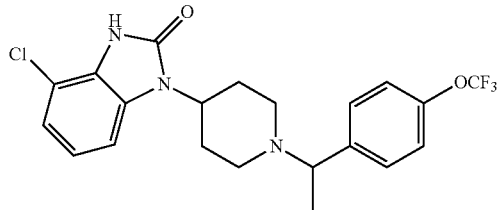 [SMILES: CC(c1ccc(OC(F)(F)F)cc1)N1CCC(n2c(=O)[nH]c3c(Cl)cccc32)CC1]

This compound was made according to the method of Example 12, using 1-(4-(difluoromethoxy)phenyl)ethanone in the final step. The overall yield was 33%.

Supporting data for the product of Example 20 includes: MS(m/z): [M+H] calc'd for $C_{21}H_{23}ClF_2N_3O_2$, 422.1; found, 422.1.

Example 21

6-chloro-1-(1-(1-(4-chloro-2-fluorophenyl)ethyl)piperidin-4-yl)-1H-benzo[d]imidazol-2(3H)-one

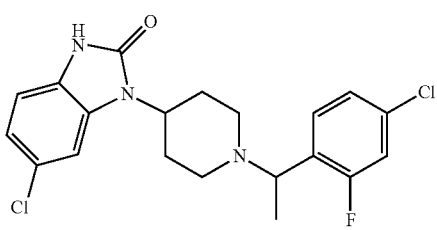 [SMILES: CC(c1ccc(Cl)cc1F)N1CCC(n2c(=O)[nH]c3ccc(Cl)cc32)CC1]

This compound was made according to the method of Example 6, using 1-(4-chloro-2-fluorophenyl)ethanone in the final step. The overall yield was 30%.

Supporting data for the product of Example 21 includes: MS(m/z): [M+H] calc'd for $C_{20}H_{21}Cl_2FN_3O$, 408.1; found, 408.1.

Example 22

6-bromo-1-(1-(1-(4-(trifluoromethoxy)phenyl)ethyl)piperidin-4-yl)-1H-benzo[d]imidazol-2(3H)-one

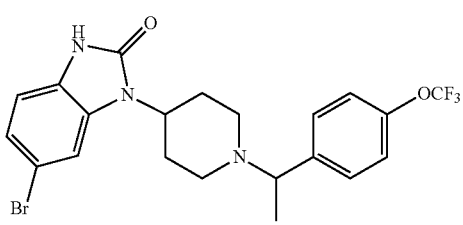 [SMILES: CC(c1ccc(OC(F)(F)F)cc1)N1CCC(n2c(=O)[nH]c3ccc(Br)cc32)CC1]

This compound was made according to the method of Example 8, using 1-(4-(trifluoromethoxy)phenyl)ethanone in the final step. The overall yield was 33%.

Supporting data for the product of Example 22 includes: MS(m/z): [M+H] calc'd for $C_{21}H_{22}BrF_3N_3O_2$, 486.1 and 484.1; found 486.1 and 484.1.

Example 23

6-bromo-1-(1-(1-(4-chloro-2-fluorophenyl)ethyl)piperidin-4-yl)-1H-benzo[d]imidazol-2(3H)-one

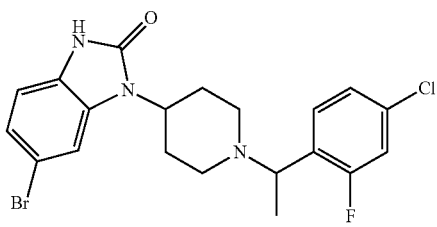 [SMILES: CC(c1ccc(Cl)cc1F)N1CCC(n2c(=O)[nH]c3ccc(Br)cc32)CC1]

This compound was made according to the method of Example 8, using 1-(4-chloro-2-fluorophenyl)ethanone in the final step. The overall yield was 28%.

Supporting data for the product of Example 23 includes: MS(m/z): [M+H] calc'd for $C_{20}H_{21}BrClFN_3O$, 454.0 and 452.0; found 454.1 and 452.1.

Example 24

4,6-dichloro-1-(1-(1-(4-methoxyphenyl)ethyl)piperidin-4-yl)-1H-benzo[d]imidazol-2(3H)-one

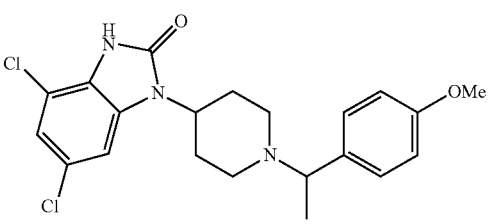 [SMILES: COc1ccc(C(C)N2CCC(n3c(=O)[nH]c4c(Cl)cc(Cl)cc43)CC2)cc1]

This compound was made according to the method of Example 1, but using 1,5-dichloro-3-fluoro-2-nitrobenzene as the starting material in step 1, and using 1-(4-methoxyphenyl)ethanone in the final step while using procedure B, with titanium (IV) isopropoxide added prior to the addition of the reducing agent, which was in this case NaBH$_3$CN. The overall yield was 21%.

Supporting data for the product of Example 24 includes: [M+H] calc'd for $C_{21}H_{24}Cl_2N_3O_2$, 420.1; found 420.1.

Example 25

5,6-dichloro-1-(1-(2-fluoro-4-methylbenzyl)piperidin-4-yl)-1H-benzo[d]imidazol-2(3H)-one

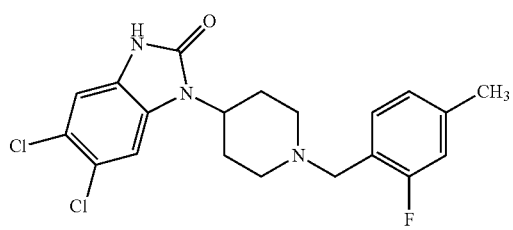 [SMILES: Cc1ccc(CN2CCC(n3c(=O)[nH]c4cc(Cl)c(Cl)cc43)CC2)c(F)c1]

This compound was made according to the method of Example 1, using 2-fluoro-4-methylbenzaldehyde in step 5. The overall yield was 32%.

Supporting data for the product of Example 25 includes: [M+H] calc'd for $C_{20}H_{21}Cl_2FN_3O$, 408.1; found 408.2. $^1$H NMR of the mesylate salt (400 MHz, MeOD) δ 7.54-7.50 (m, 2H), 7.22-7.15 (m, 3H), 4.56 (tt, J=12.2, 4.0 Hz, 1H), 4.43 (s, 2H), 3.70 (d, J=12.8 Hz, 2H), 3.35-3.29 (m, 2H), 2.82-2.71 (m, 8H), 2.44 (s, 3H), 2.10 (d, J=14.4 Hz, 2H); HPLC $t_R$=3.692 min (HPLC method 1); purity >90%.

Compounds of the invention may also be prepared as described in the General Reaction Scheme 2 shown below:

General Scheme 2

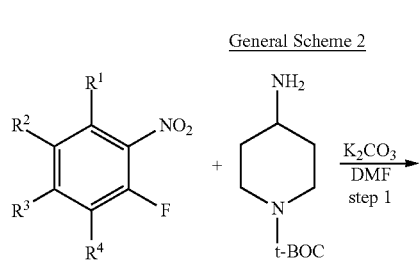

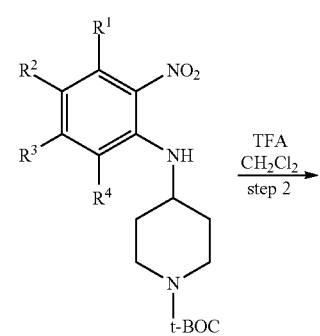

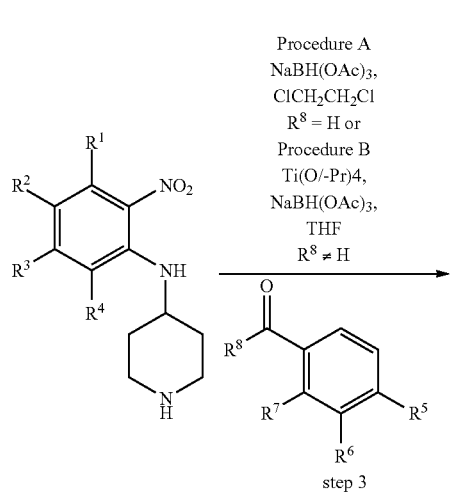

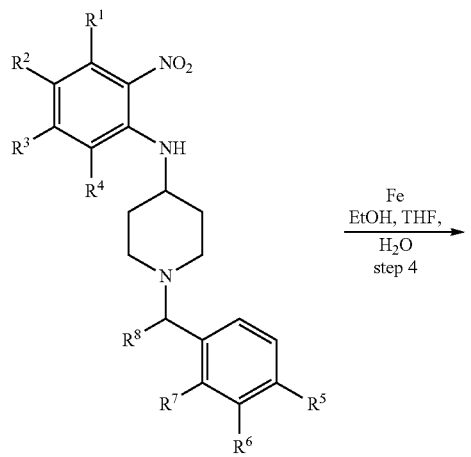

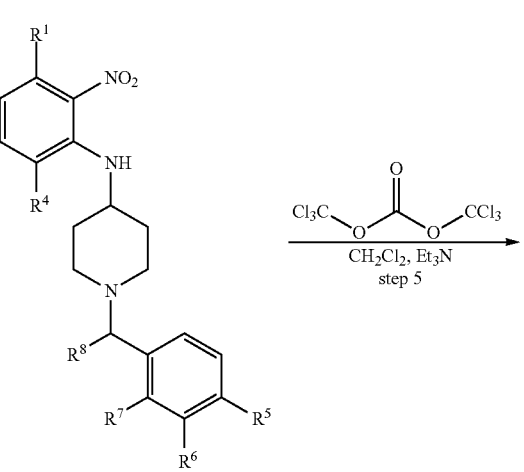

The following compounds were made according to the methods of General Scheme 2:

TABLE 2

| example | structure | R groups | step 3 reaction conditions | identification numbers |
|---|---|---|---|---|
| 26 | 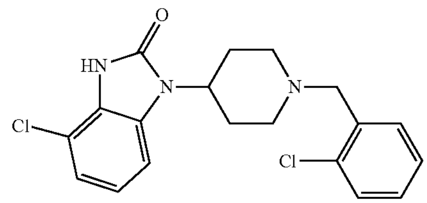 [SMILES: O=c1[nH]c2c(Cl)cccc2n1C1CCN(Cc2ccccc2Cl)CC1] | $R^1 = R^7 = Cl$, other R groups = H | Procedure A, NaBH(OAc)$_3$ | S112.001 SR-11099 |
| 27 | 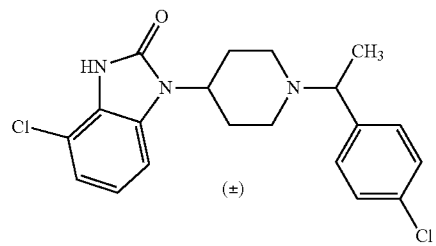 [SMILES: CC(c1ccc(Cl)cc1)N1CCC(n2c(=O)[nH]c3c(Cl)cccc32)CC1] | $R^1 = R^7 = Cl$, $R^8 = Me$, other R groups = H | Procedure B, Ti(Oi-Pr)$_4$, NaBH(OAc)$_3$ | S112.027 SR-11964 |

Example 26

4-chloro-1-(1-(2-chlorobenzyl)piperidin-4-yl)-1H-benzo[d]imidazol-2(3H)-one

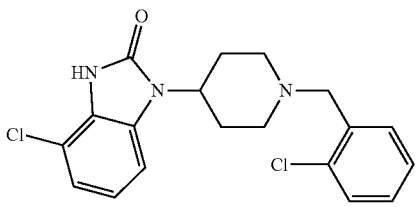 [SMILES: O=c1[nH]c2c(Cl)cccc2n1C1CCN(Cc2ccccc2Cl)CC1]

Step 1. Follows step 1 of Example 1, except that the solvent was DMF, while 1-chloro-3-fluoro-2-nitrobenzene was used as the starting material. This provided tert-butyl 4-((3-chloro-2-nitrophenyl)amino)piperidine-1-carboxylate as the product. The yield was 93%.

Step 2. Follows step 4 of Example 1, treatment with TFA:CH$_2$Cl$_2$, using the product of step 1 (this example), tert-butyl 4-((3-chloro-2-nitrophenyl)amino)piperidine-1-carboxylate, as the starting material and providing N-(3-chloro-2-nitrophenyl)piperidin-4-amine as the product. The yield of the crude material, taken to the next step without chromatographic purification, was 88%.

Step 3. Follows step 5 of Example 1, the NaBH(OAc)$_3$-promoted reductive alkylation reaction, using the product of step 2 (this example), N-(3-chloro-2-nitrophenyl)piperidin-4-amine, and 2-chlorobenzaldehyde as the starting materials and giving N-(3-chloro-2-nitrophenyl)-1-(2-chlorobenzyl)piperidin-4-amine as the product, after purification by column chromatography using 15:85 hexane:ethyl acetate containing 0.1% Et$_3$N as eluent. The yield was 91%.

Step 4. The product of step 3, N-(3-chloro-2-nitrophenyl)-1-(2-chlorobenzyl)piperidin-4-amine (379 mg, 1 mmol), was dissolved in 3 mL of a 1:2:6 solvent mixture of water:THF:ethanol. Iron powder (450 mg, 8 mmol, 8 equiv.) was added in one portion. The solution was stirred at room temperature overnight. The mixture was diluted with ethyl acetate (5 mL) and this solution was filtered through Celite® and the pad was washed with ethanol (3×5 mL). The solution was concentrated under reduced pressure. Purification was achieved by flash column chromatography on silica gel using 2% to 10% gradient of hexane in ethyl acetate containing 0.1% Et$_3$N as eluent. Fractions containing the desired product were pooled and concentrated under reduced pressure to give the product as an oil. 231 mg of the product 3-chloro-N$^1$-(1-(2-chlorobenzyl)piperidin-4-yl)benzene-1,2-diamine (66%).

Step 5. A portion of the product of step 3, 3-chloro-N$^1$-(1-(2-chlorobenzyl)piperidin-4-yl)benzene-1,2-diamine (118 mg, 0.34 mmol), was dissolved in dichloromethane (5 mL). Et$_3$N (130 µL, 94 mg, 0.93 mmol, 2.7 equiv.) was added, followed by triphosgene (45 mg, 0.15 mmol). The solution was stirred at room temperature for 3 hours. The solvent was removed under reduced pressure and the residue was dissolved in ethyl acetate (5 mL).

This solution was washed with cold 1M HCl (2×2 mL) and water (2×2 mL). The organic layer was dried using MgSO$_4$ and the solvent was removed under reduced pressure. Purification was achieved by flash column chromatography on silica gel using a gradient of 0-20% methanol in dichloromethane as eluent, with each solvent containing 0.1% Et$_3$N. Fractions containing the desired product were pooled and concentrated under reduced pressure to give the product as a yellow oil. 102 mg of the product 4-chloro-1-(1-(2-chlorobenzyl)piperidin-4-yl)-1H-benzo[d]imidazol-2(3H)-one was obtained (81%).

Supporting data for the product of Example 26 includes: $^1$H NMR (400 MHz, MeOD) δ 7.71 (dd, J=7.40, 1.92, 1H), 7.62 (dd, J=8.00, 1.55, 1H), 7.57-7.47 (m, 2H), 7.22 (dd, J=7.02, 1.86, 1H), 7.11-7.03 (m, 2H), 4.65-4.55 (m, 3H), 3.73 (d, J=12.04, 2H), 3.43 (t, J=12.26, 2H), 2.81 (d, J=13.31, 2H), 2.09 (d, J=14.80, 2H), MS(m/z): [M+H] calc'd for C$_{19}$H$_{19}$Cl$_2$N$_3$O 376.1, 378.1, found 376.2, 378.1. HPLC t$_R$=3.49 min (HPLC method 1); purity=99.9%.

Example 27

4-chloro-1-(1-(1-(4-chlorophenyl)ethyl)piperidin-4-yl)-1H-benzo[d]imidazol-2(3H)-one

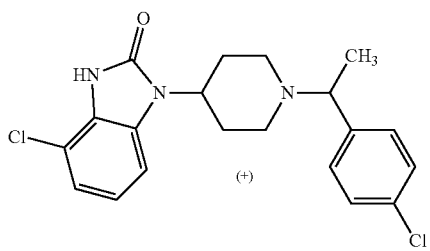 [SMILES: CC(c1ccc(Cl)cc1)N1CCC(n2c(=O)[nH]c3c(Cl)cccc32)CC1]

(+)

Step 1 and 2: repeats steps 1 and 2 of Example 26.

Step 3. Follows step 5 of Example 2, the procedure using Ti(Oi-Pr)$_4$ and NaBH(OAc)$_3$, with N-(3-chloro-2-nitrophenyl)piperidin-4-amine and 1-(4-chlorophenyl)ethanone as the starting materials and providing N-(3-chloro-2-nitrophenyl)-1-(1-(4-chlorophenyl)ethyl)piperidin-4-amine as the product. The yield was 87%.

Steps 4 and 5. Follows steps 4 and 5 of Example 26, beginning with N-(3-chloro-2-nitrophenyl)-1-(1-(4-chlorophenyl)ethyl)piperidin-4-amine and providing 4-chloro-1-(1-(1-(4-chlorophenyl)ethyl)piperidin-4-yl)-1H-benzo[d]imidazol-2(3H)-one as the product. The yield was 52% for two steps.

Supporting data for the product of Example 27 includes: $^1$H NMR (400 MHz, MeOD) δ 7.61-7.50 (m, 4H), 7.21 (dd, J=7.08, 1.64, 1H), 7.11-7.00 (m, 2H), 4.57 (q, J=6.64, 1H), 4.52-4.41 (m, 1H), 3.88 (d, J=11.44, 1H), 3.52 (d, J=12.96, 1H), 3.20-2.98 (m, 2H), 2.93-2.7 (m, 2H), 2.16-1.96 (m, 2H), 1.81 (d, J=6.96, 3H). MS(m/z): [M+H] calc'd for C$_{20}$H$_{21}$Cl$_2$N$_3$O 390.1, 392.1, found 390.2, 392.1. HPLC t$_R$=3.71 min (HPLC method 1); purity=99.9%.

Anticipated procedural variations for Examples 26-27: The reagents used in these methods are fully suited for the indicated syntheses but an experimentalist is not limited to the described reagents and/or reaction conditions, as one of ordinary skill may recognize other suitable reagents and/or reaction conditions. Specific common variants are here specified: While tert-butyl 4-aminopiperidine-1-carboxylate was used as the starting material, other N$^1$-protecting groups on the 4-aminopiperidine reactant can instead be used, with a corresponding adjustment in how step 2 (protecting group removal) is conducted. Bases and solvents other than the indicated EtN(i-Pr)$_2$ in DMF method are suitable for use in step 1. Other reaction conditions and/or reducing agents may be used in step 3 to form the indicated products. Reducing conditions other than the indicated combination of iron powder in acetic acid can be used for nitro group reduction in step 4. Reagents other than triphosgene can be used in step 5 to form the benzimidazolone ring, including a phosgene solution or carbonyl diimidazole. Purification methods other than flash chromatography may alternatively be used (e.g., preparative HPLC, recrystallization, etc.).

Compounds of the invention may also be prepared as described in the General Reaction Scheme 3 shown below:

General Scheme 3

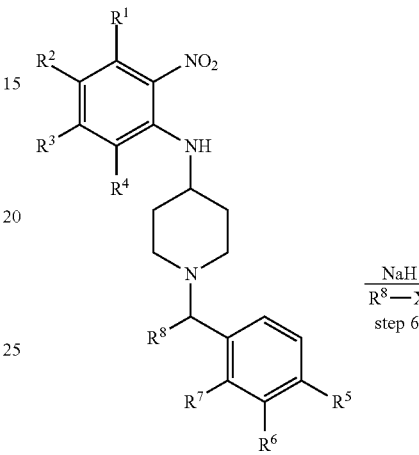

prepared as in
General Scheme 1 or
General Scheme 2
steps 1-5

The following compounds were made according to the method of General Scheme 3:

TABLE 3

| example | structure | R groups | step 6 reaction conditions | identification numbers |
|---|---|---|---|---|
| 28 | 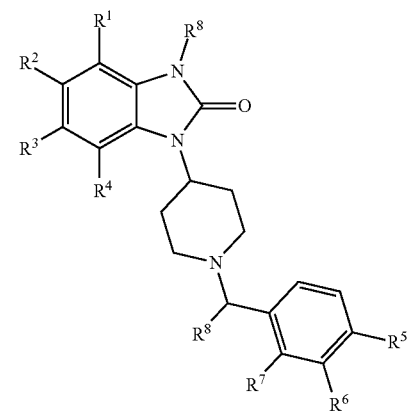 | R$^2$ = Me, R$^7$ = Cl, R$^8$ = CH$_2$-cyclopropyl, other R groups = H | NaH, DMF, (bromomethyl) cyclopropane | S112.006 SR-11427 |

TABLE 3-continued

| example | structure | R groups | step 6 reaction conditions | identification numbers |
|---|---|---|---|---|
| 29 | 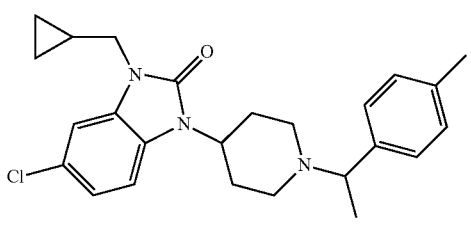 | $R^2$ = Cl, $R^5$ = Me, $R^7$ = Me, $R^8$ = $CH_2$-cyclopropyl, other R groups = H | NaH, DMF, (bromomethyl) cyclopropane | S86.020 SR-11712 |

Example 28

1-(1-(2-chlorobenzyl)piperidin-4-yl)-3-(cyclopropylmethyl)-5-methyl-1H-benzo[d]imidazol-2(3H)-one

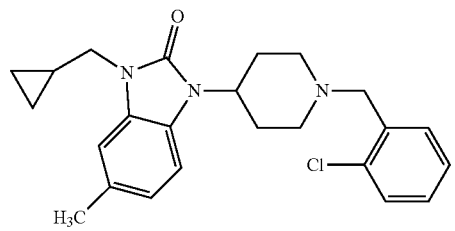 [SMILES: Cc1ccc2c(c1)n(CC1CC1)c(=O)n2C1CCN(Cc2ccccc2Cl)CC1]

Steps 1-5. The compound 1-(1-(2-chlorobenzyl)piperidin-4-yl)-5-methyl-1H-benzo[d]imidazol-2(3H)-one was made following the methods of General Scheme 2 for steps 1-5, using 1-fluoro-4-methyl-2-nitrobenzene in step 1 and 4-chlorobenzaldehyde in step 3. The overall yield for the 5 step route was 41%.

Step 6. To the product of step 5 (18.0 mg, 0.05 mmol) in DMF (2 mL) was added 50% NaH in mineral oil (20 mg, 10 mg NaH, 0.42 mmol, 8 equiv.) and (bromomethyl)cyclopropane (24.3 mg, 0.18 mmol, 3.6 equiv.). The solution was stirred at room temperature for 4 hours. Water (5 mL) was added, followed by ethyl acetate (5 mL). The organic layer was separated and the aqueous layer was extracted with ethyl acetate (2×5 mL). The combined organic layers were dried using $MgSO_4$ and the solvent was removed under reduced pressure. Purification was achieved by flash column chromatography on silica gel using a gradient of 0-20% methanol in dichloromethane as eluent, with each solvent containing 0.1% $Et_3N$. Fractions containing the desired product were pooled and concentrated under reduced pressure to give the product as a light yellow oil. This oil was dissolved in a minimal amount of water-acetonitrile (1:1). Trifluoroacetic acid (15 µL) was added. The solution was frozen and subjected to lyophilization overnight, giving the product as a tan solid, in the form of a trifluoroacetic acid salt. 13.2 mg of the product 1-(1-(2-chlorobenzyl)piperidin-4-yl)-3-(cyclopropylmethyl)-5-methyl-1H-benzo[d]imidazol-2(3H)-one (trifluoroacetic acid salt) was obtained (64%).

Supporting data for the product of Example 28 includes: MS(m/z): [M+H] calc'd for $C_{24}H_{28}ClN_3O$ 410.2, found 410.2. HPLC $t_R$=4.09 min (HPLC method 1); purity=99.9%.

Example 29

5-chloro-3-(cyclopropylmethyl)-1-(1-(1-(p-tolyl)ethyl)piperidin-4-yl)-1H-benzo[d]imidazol-2(3H)-one This compound was made following the methods of Example 28. General Scheme 2 was used for steps 1-5, using 1-fluoro-4-chloro-2-nitrobenzene in step 1 and 4-methylacetophenone in the reductive amination step, with titanium isopropoxide and $NaBH_3CN$ used. The overall yield for the 5 step route was 27%.

Supporting data for the product of Example 29 includes: MS(m/z): [M+H] calc'd for $C_{25}H_{31}ClN_3O$ 424.2, found 424.2.

Anticipated procedural variations for Examples 29-30: The reagents used in these methods are fully suited for the indicated synthesis but an experimentalist is not limited to the described reagents and/or reaction conditions, as one of ordinary skill may recognize other suitable reagents and/or reaction conditions. Strong bases other than sodium hydride may be used in step 6. Examples of such suitable bases include $LiN(i-Pr)_2$, $LiN(SiMe_3)_2$, and KOt-Bu. The choice of conditions may vary depending upon the properties of both the benzimidazolone substrate and the electrophile $R^8$—X. Purification methods other than flash chromatography may alternatively be used (e.g., preparative HPLC, recrystallization, etc.).

Biological Assessment Methods

In Vitro Pharmacology Assays:

G protein signaling assays: A standard [$^{35}$S]GTPγS binding assay in membranes prepared from CHO cells expressing the human MOR was performed in a concentration response manner. All compounds were run in parallel with DAMGO and morphine.

cAMP inhibition assays: The CisBio cAMP cell based assay kit that uses HTRF technology was utilized to assess MOR-mediated inhibition of cAMP. Assays were performed according to manufacturer's instructions, in the presence of 20 μM forskolin and 25 μM PDE-IV. All compounds were run in parallel with DAMGO and morphine.

βarrestin2 recruitment assays: The commercial enzyme fragment complementation assay "PathHunter®" from DiscoveRx, Fremont Calif., was used to assess recruitment of βarrestin2 to the human MOR in U2OS cells. Assays were performed according to manufacturer's instructions. All compounds were run in parallel with DAMGO and morphine.

MOR phosphorylation assays: HAmMOR HEK cells were treated with drug for 10 minutes and then the receptor was immunoprecipitated using anti-HA agarose beads. MOR phosphorylation at serine375 was determined by immunoblotting with the Cell Signaling antibody.

Bias Analysis:

Bias calculations were made by applying the dose response data, obtained from experiments run in parallel with the reference ligand, to the operational model as defined by Black and Leff (25) as modified for Prism software, GraphPad, (La Jolla, Calif.), and applied as presented by Kenakin and Christopoulos (27). The relative activity of an agonist in each assay is simultaneously compared to the relative activity of the reference compound, in this case DAMGO, and following mathematically transformation, a normalization of the potential of the test compound to produce a response is garnered in the form of the "transduction coefficient" or the $\Delta \text{Log}(\tau/K_A)$ or $\Delta \text{Log R}$ as represented in the program. Comparison of the performance of the compound across two assays can be made to generate a $\Delta\Delta \text{Log}(\tau/K_A)$ or the "Bias Factor," the latter term is used in this report. A higher "Bias Factor" indicates a greater performance of a test compound compared to DAMGO in one assay over another (i.e., G protein/βarrestin2).

Antinociception:

The mouse hot plate test and warm water tail immersion test have been extensively described and have been used to assess antinociceptive drug properties; all opioid analgesics that are potent in humans induce antinociception in these mouse pain assays. The mouse hot plate (Columbus Instruments, Columbus, Ohio) was set to a steady temperature of 52° C. Baseline response latencies were established prior to drug treatment (approximately 6 seconds). A response was considered any motion indicating an attempt to remove a paw from the hot surface. A similar approach was taken in the mouse warm water tail immersion (tail flick) test. Water temperature was maintained at 49° C. producing a baseline latency for response (flicking or removing the tail from the water) of approximately 3 seconds. For both tests, drugs were administered systemically (in many cases, tested both i.p. and s.c.) and response latencies were measured every 30 minutes for up to 6 hours. Antinociception was observed when the response latencies were significantly greater than baseline measures ($\alpha=0.05$, t-test or ANOVA). In each type of experiment a time cutoff was imposed to prevent injury, in accord with regulations for animal care (approved IACUC protocols) in such experiments.

Biological Activity of Representative Compounds of the Invention

Example 30

The following table summarizes the biological activity of specific claimed compounds that were described in the Examples.

TABLE 4

| # | ID numbers | G protein coupling (GTPγS assay) | | | bias factor G/βarr2 | G protein coupling (cAMP assay) | | bias factor G/βarr2 | anti-nociceptive activity in vivo (mice) | in vivo models assessed |
|---|---|---|---|---|---|---|---|---|---|---|
| | | $EC_{50}$ (nM) | $E_{max}$ (%) | $\Delta\Delta\tau/KA$ GTPγS | | $EC_{50}$ (nM) | $E_{max}$ (%) | $\Delta\Delta\tau/KA$ cAMP | | |
| 1 | S186 SR-14249 | 67 | 43 | >10 | | 89 | 105 | >10 | yes | hot plate & tail flick |
| 2 | S186.002 SR-14963 | 16 | 83 | 6.7 | | 7 | 99 | 1.6 | not tested | |
| 3 | S86.025 SR-12968 | 43 | 71 | >10 | | 30 | 103 | 8.7 | yes | hot plate & tail flick, respiratory suppression |
| 4 | S86.033 SR-14152 | 223 | 65 | 9.6 | | 319 | 110 | 2.3 | yes | hot plate & tail flick, respiratory suppression, whole gut transit, locomotor activity |
| 5 | S86.014 SR-11503 | 291 | 28 | 5.8 | | 622 | 81 | 1.3 | not tested | |
| 6 | S112.061 SR-14167 | 2.0 | 94 | >10 | | 1 | 101 | 4.3 | not tested | |
| 7 | S86.023 SR-11794 | 33 | 83 | 8.8 | | 25 | 106 | 3.4 | yes | hot plate & tail flick, whole gut transit |
| 8 | S112.082 SR-14979 | 2.5 | 95 | >10 | | 1 | 105 | >10 | not tested | |
| 9 | S112.064 SR-14220 | 45 | 88 | 6.2 | | 35 | 109 | 2.6 | not tested | |
| 10 | S86.037 SR-14219 | 279 | 73 | 5.3 | | 258 | 98 | 1.5 | not tested | |

TABLE 4-continued

| # | ID numbers | G protein coupling (GTPγS assay) $EC_{50}$ (nM) | $E_{max}$ (%) | bias factor G/βarr2 ΔΔτ/KA GTPγS | G protein coupling (cAMP assay) $EC_{50}$ (nM) | $E_{max}$ (%) | bias factor G/βarr2 ΔΔτ/KA cAMP | anti-nociceptive activity in vivo (mice) | in vivo models assessed |
|---|---|---|---|---|---|---|---|---|---|
| 11 | S86.013 SR-11502 | 13 | 91 | 4.4 | 10 | 102 | 1.6 | yes | hot plate & tail flick |
| 12 | S112.062 SR-14206 | 2.3 | 93 | 4.2 | 1 | 105 | 2.2 | not tested | |
| 13 | S112.049 SR-13406 | 19 | 91 | 3.4 | 4 | 98 | 3.1 | yes | hot plate & tail flick |
| 14 | S186.004 SR-15098 | 116 | 62 | >10 | 112 | 104 | 8.1 | yes | hot plate & tail flick, respiratory suppression, whole gut transit |
| 15 | S186.005 SR-15099 | 144 | 73 | >10 | 92 | 101 | >10 | yes | hot plate & tail flick, respiratory suppression, whole gut transit, locomotor activity |
| 16 | S186.006 SR-17018 | 122 | 68 | >10 | 83 | 106 | >10 | yes | hot plate & tail flick |
| 17 | S112.084 SR-16299 | 58 | 93 | 3.1 | not tested | | | not tested | |
| 18 | S112.086 SR-16301 | 140 | 92 | 7.4 | 119 | 103 | 2.0 | not tested | |
| 19 | S86.026 SR-13403 | 15 | 89 | 4.0 | not tested | | | not tested | |
| 20 | S112.034 SR-12032 | 30 | 98 | 3.1 | not tested | | | not tested | |
| 21 | S112.041 SR-12038 | 14 | 91 | 3.6 | 3 | 96 | 4.1 | yes | hot plate & tail flick |
| 22 | S112.076 SR-14973 | 39 | 100 | 3.3 | not tested | | | not tested | |
| 23 | S112.077 SR-14974 | 21 | 102 | 3.4 | not tested | | | not tested | |
| 24 | S184 SR-12306 | 0.4 | 94 | 4.6 | 0.4 | 107 | 1.5 | not tested | |
| 25 | S186.011 SR-18586 | 66 | 77 | 3.0 | 32 | 104 | 1.9 | not tested | |
| 26 | S112.001 SR-11099 | 36 | 94 | 4.0 | 55 | 116 | 1.1 | not tested | |
| 27 | S112.027 SR-11964 | 3.1 | 89 | 5.0 | 3 | 108 | 1.6 | not tested | |
| 28 | S112.006 SR-11427 | 558 | 88 | 4.4 | 253 | 103 | 2.7 | not tested | |
| 29 | S86.020 SR-11712 | 12 | 83 | 3.3 | not tested | | | not tested | |

In Vivo Pharmacology Studies in Mice, Demonstrating Antinociceptive Efficacy and Attenuated Side Effects Example 31: Analgesic Potencies, Expressed by Area Under the Curve Analysis, for Selected Compounds Compared to Morphine Sulfate in the Hot Plate (52° C.) and Warm Water (49° C.) Tail Immersion (Tail Flick) Tests The identification numbers shown correspond to those in column 2 of Table 4 and can readily be cross-referenced to the corresponding synthesis Example.

Figure 3B:
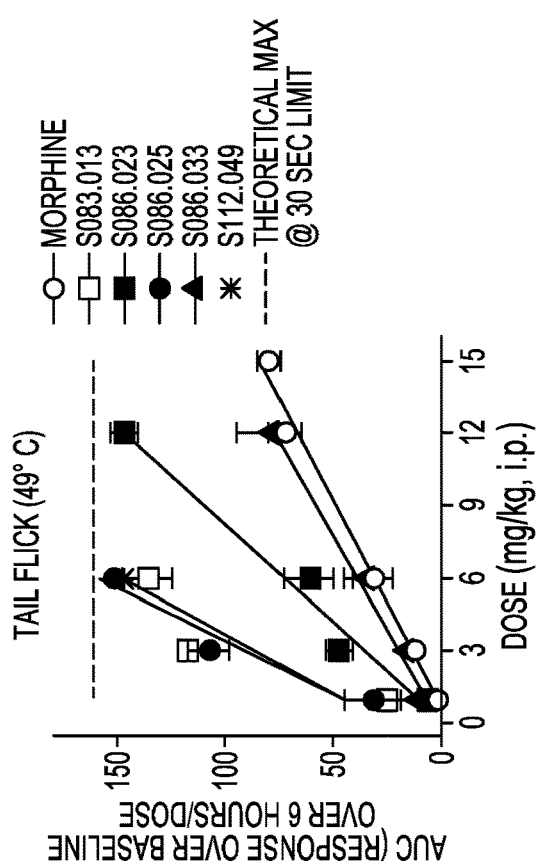
FIG. 3 is a graphic representation of the data obtained in Example 31, showing the analgesic potencies, expressed by area under the curve analysis, for selected compounds compared to morphine sulfate in the hot plate (52° C.) and warm water (49° C.) tail immersion (tail flick) tests.
Figure 3A:
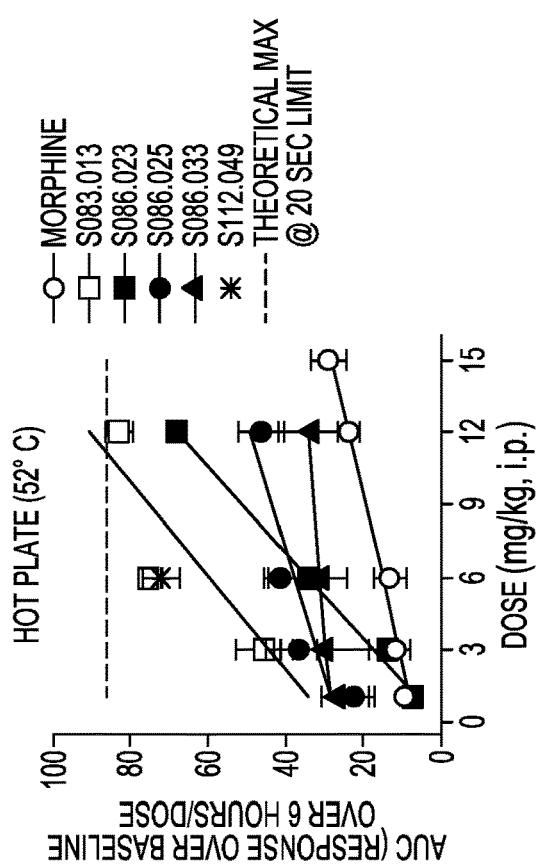
Figure 5A:
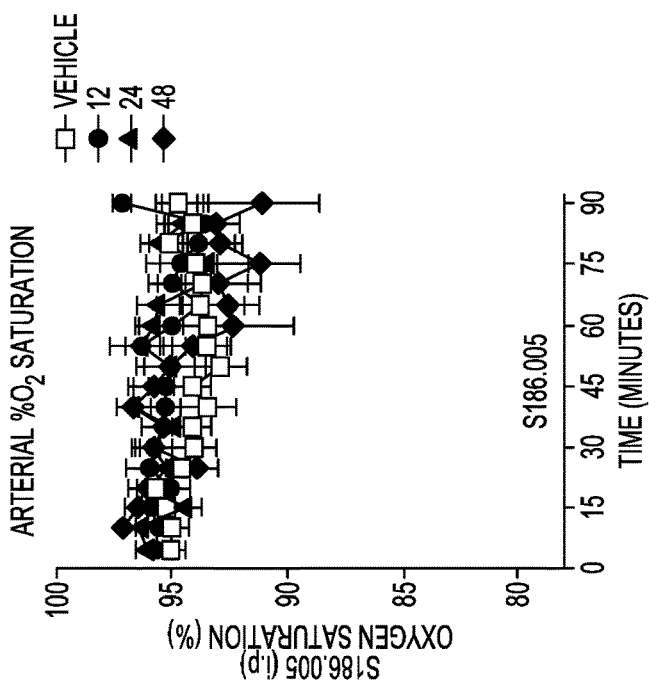
FIG. 5 is a graphic representation of data obtained in Example 33.1, the time course representations of the data acquired.
Figure 5B:
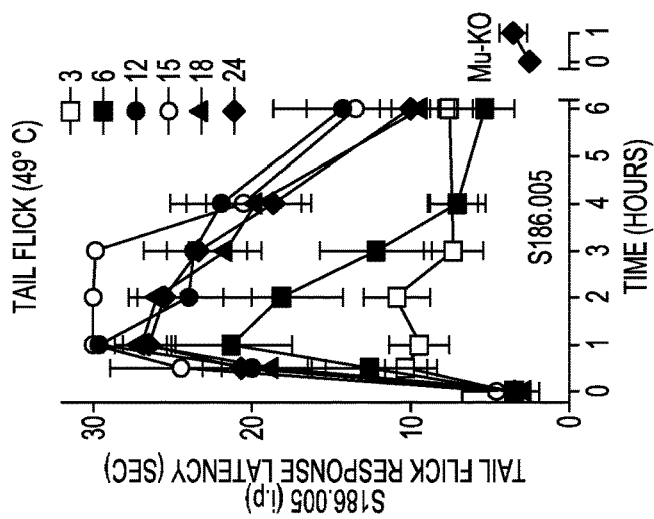
Figure 5C:
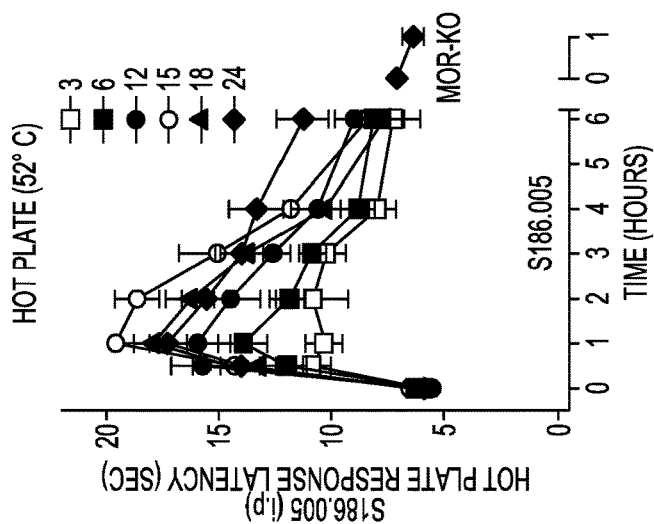
Figure 5F:
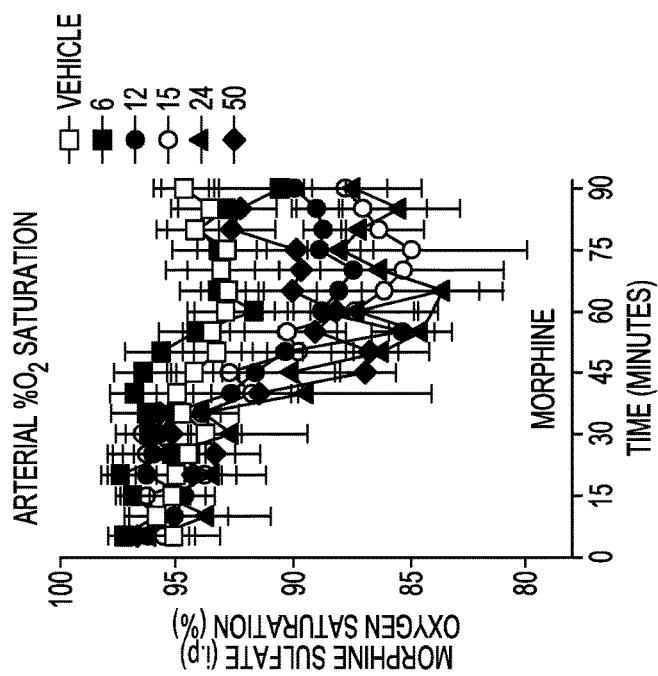
Figure 5E:
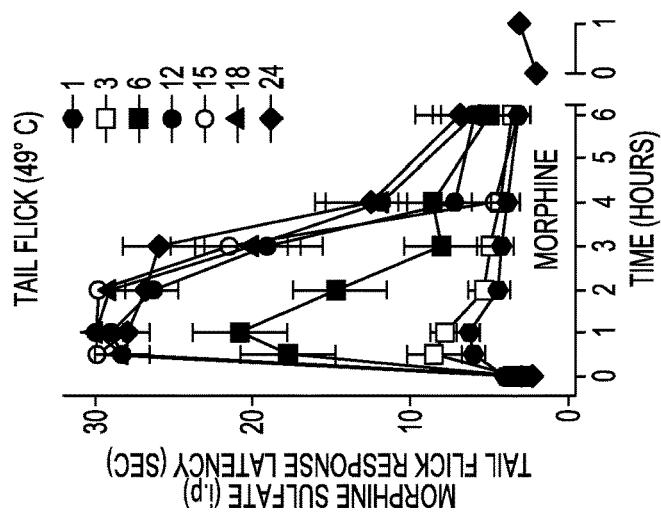
Figure 5D:
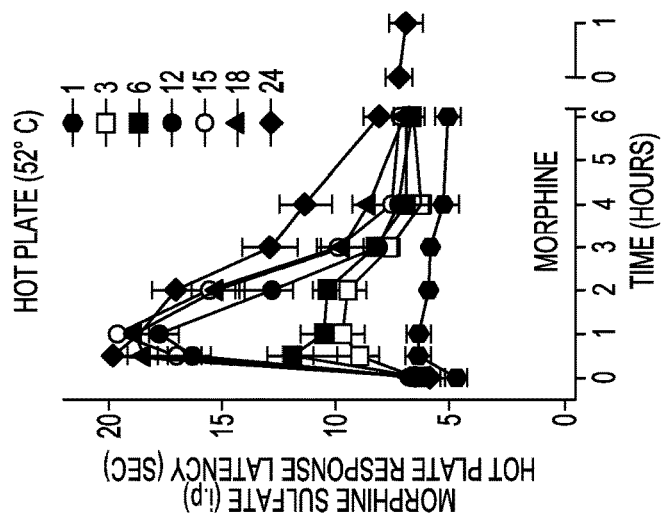

All results were analyzed by subtracting baselines and establishing area under the curve analysis over a 6 hour time frame. A 20 second max was applied to the hot plate and a 30 second max was applied to the tail flick assay to prevent injury. All doses were prepared as base weight of TSRI compounds and the salt weight of morphine sulfate. Results are shown in FIG. 3. Identification of the compounds is as follows: S086.013=the product of Example 11; S086.023=the product of Example 9; S086.025=the product of Example 3; S086.033=the product of Example 4; and S112.049=the product of Example 13.

Example 32: Antinociception and Constipation Induced by Compound S086.025 (the Product of Example 3), Following Acute and Following Chronic Administration S086.025 (G/βarr2 bias factor >10, using the [$^{35}$S]GTPγS binding assay) induces robust antinociception that is more pronounced and that also lasts longer than morphine sulfate in both the hot plate (52° C.) and warm water (49° C.) tail immersion (tail flick) tests. Area under the curve analysis for this compound is shown in Example 31 (orange filled circles). In a separate cohort of animals, fecal boli production was evaluated after a 3 mg/kg s.c. dose of S086.025; this was compared to a near equianalgesic dose of morphine sulfate (6 mg/kg, s.c. in tail flick tests; analgesic data is not shown for s.c. dosing, however it was very similar to that seen following i.p. dosing). Following acute administration, both morphine and S086.025 induced constipation. However, following chronic administration of S086.025, (3 mg/kg every 12 hours for 3 days, then 6 mg/kg every 12 hours for 2 days), mice were again tested for constipation (post chronic, 3 mg/kg, s.c.). The animals treated chronically with S086.025 ceased responding to the drug relative to control, suggesting that constipation no longer occurs. In the same cohort of animals, baseline responses in the hot plate test were taken after the 6 hour boli collection and then a second challenge dose of S086.025 (6 mg/kg, s.c.) was given. Antinociceptive responses taken at one hour were not different between the acute treatment group and the group that had received chronic drug treatment. These findings suggest that the mice become rapidly desensitized to the acute constipating effects of S086.025, but they do not become desensitized to the antinociceptive effects, suggesting that constipation and analgesic efficacy can be separated by using this biased mu opioid agonist. The predominant cause of persistent constipation is due to non-tolerizing opioid agonism in the colon; while the upper GI effects do wane overtime. The Bohn lab has proposed the hypothesis that βarrestins mediate opioid-induced constipation by activating MOR in the colon per se (17). Results are shown in FIG. 4.

Figure 6C:
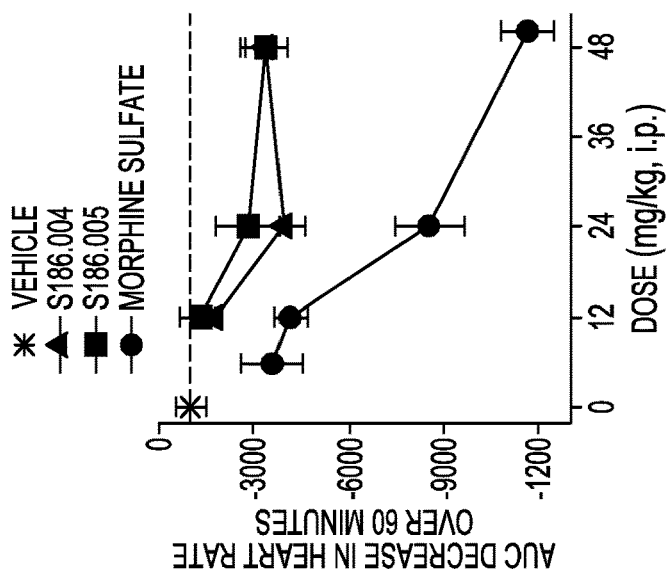
FIG. 6 is a graphic representation of data obtained in Example 33.2 showing the area under the curve analysis of the respiratory and cardiovascular responses compared to the antinociceptive responses.
Figure 6B:
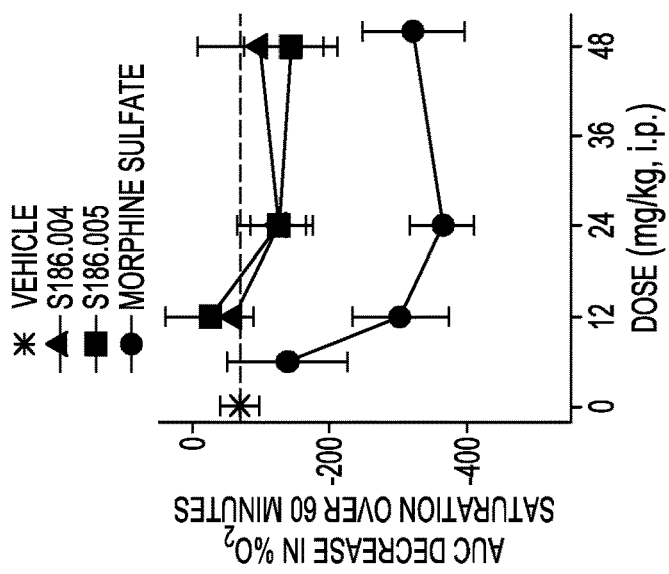
Figure 6A:
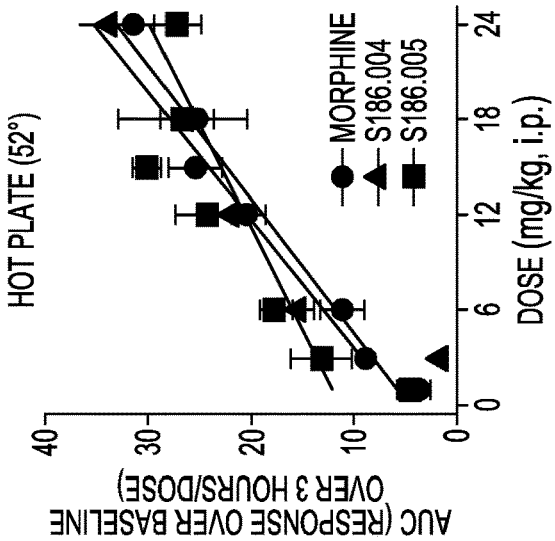
Figure 7B:
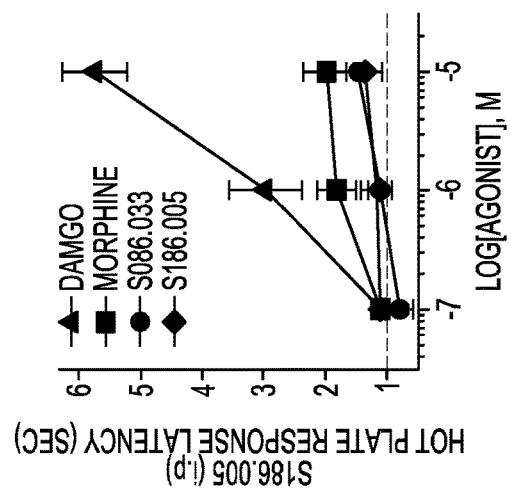
FIG. 7 depicts the results of Example 34, showing differential effects on MOR phosphorylation
Figure 7A:
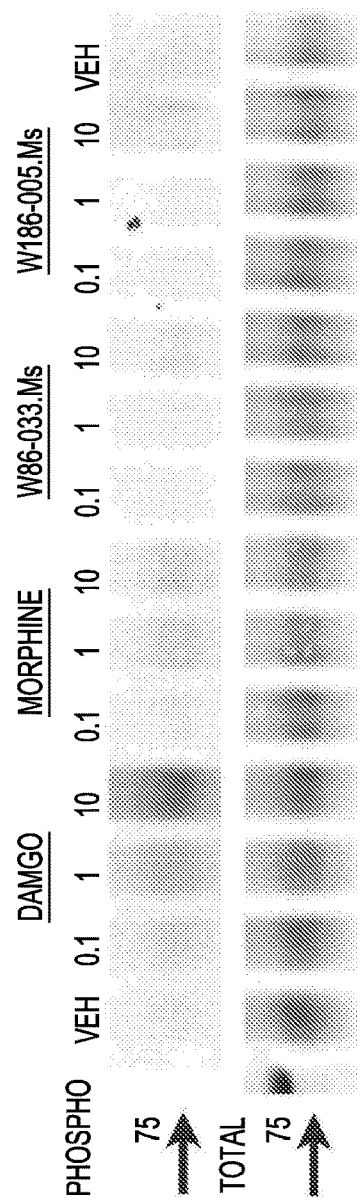
Figure 8B:
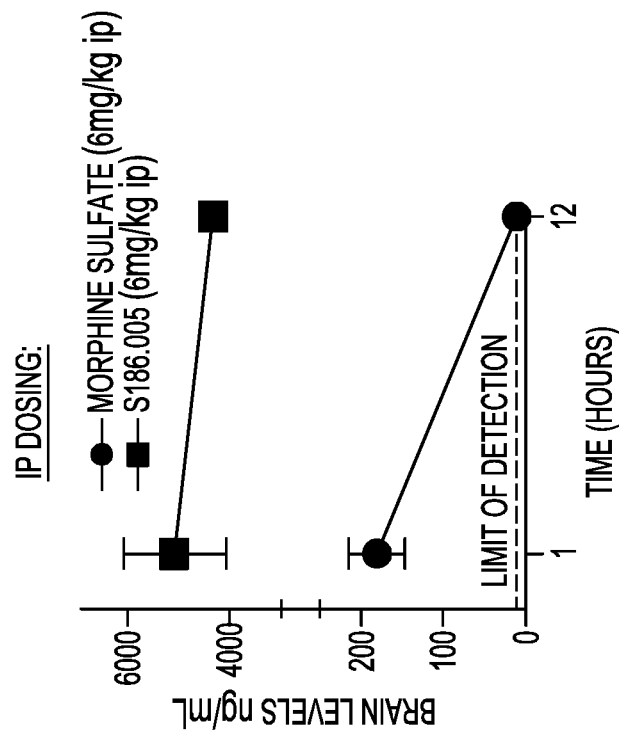
FIG. 8 depicts the results of Example 35, showing selected data regarding modes of dosing in vivo and pharmacokinetic properties. The top two panels below shows plasma and brain levels of S186.005 at various time points following i.p. dosing at 6 mg/kg. Below the plasma and brain level data is shown many standard pharmacokinetic parameters measured for morphine and for the test compound S186.005, delivered intraveneously (i.v.) at 1 mg/kg or orally (p.o.) at 3 mg/kg.
Figure 8A:
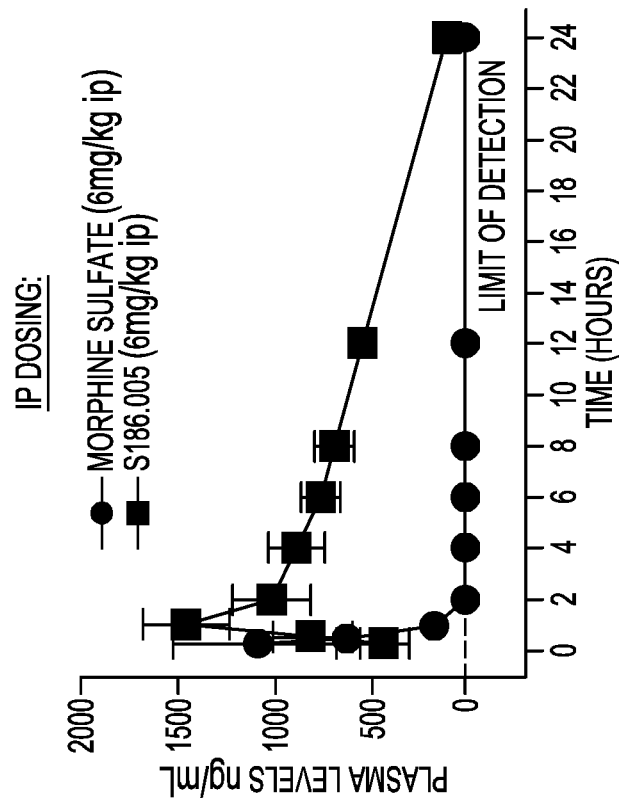

Example 33: Separation of Analgesic Efficacy and Respiratory and Cardiovascular Side Effects Antinociceptive, respiratory and cardiovascular responses to S086.033 (G/βarr2 bias factor >10) analyzed per dose over time in C57BL/6 male mice. Antinociceptive data were obtained in a 52° C. hotplate (20 sec cutoff imposed) and a 49° C. warm water tail flick test (30 sec cutoff imposed). For respiratory measures, shaved male C57BL/6 mice were habituated to conical tube restraints for 1 day prior to testing and on the test day for 1 hour and testing was performed with a MouseOx® pulse oximeter. Results are shown in FIGS. 5 and 6.

Area under the curve (AUC) analysis was performed following subtraction of baseline responses. The antinociceptive response period was 6 hours, wherein testing occurred as shown in Example 31. For respiratory and cardiology measures, mice were treated as described in Example 33.1. All parameters were simultaneously recorded. Area under the curve analysis was performed by subtracting baseline measures obtained for the first 30 minutes of data for each dose during a 1 hour test period after compound injection. At all doses tested, S086.033 produced an equal antinociceptive response equal to or exceeding that of morphine while producing results in several measured parameters (% $O_2$ saturation, respiratory frequency, heart rate) that indicate diminished or even absent side effects, in comparison to morphine. At or even above the equianalgesic dose (relative to morphine) and at or even above the maximal effective dose of ca.12 mg/kg, i.p., effects of S086.033 did not differ from that of vehicle in these respiratory or cardiovascular measures. These findings demonstrate that biased MOR agonists may be useful in producing antinociception with improved safety margins.

Example 34: Differential Effects on MOR Phosphorylation

Agonist-induced MOR phosphorylation at serine 375 was determined by immunoprecipitating the HA-MOR. DAMGO and morphine both induce phosphorylation at 1 µM concentrations. S086.033 (G/βarr bias factor=9.6) and S186-005 (G/βarr bias factor >10) only induce slight phosphorylation at 10 µM.

Example 35: Selected Data Regarding Modes of Dosing In Vivo and Pharmacokinetic Properties Compounds of the invention to be used for the relief of pain (in its many forms) may be administered by many different modes that are common in the field, such as (but not limited to) oral dosing, subcutaneous dosing, i.v. dosing, and transdermal delivery. The suitability of selected compounds of the invention for delivery to mice by various modes, including intraperitoneal (i.p) dosing is illustrated in this Example. The suitability of multiple modes of compound delivery in rodents serves to support the feasibility of various dosing strategies common in the field in higher mammals, including man.

The top two panels below shows plasma and brain levels of S186.005 at various time points following i.p. dosing at 6 mg/kg. The test compound is readily detected at multiple time points at which, in an analogous experiment, morphine administered at the same dose is not detectable.

Below the plasma and brain level data is shown many standard pharmacokinetic parameters measured for morphine and for the test compound S186.005, delivered intraveneously (i.v.) at 1 mg/kg or orally (p.o.) at 3 mg/kg. Relative to morphine, by either route of administration 5186.005 has a longer plasma half-life, reaches a higher maximum plasma concentration, has higher exposure by AUC calculations, and is cleared less rapidly.

Figure 9B:
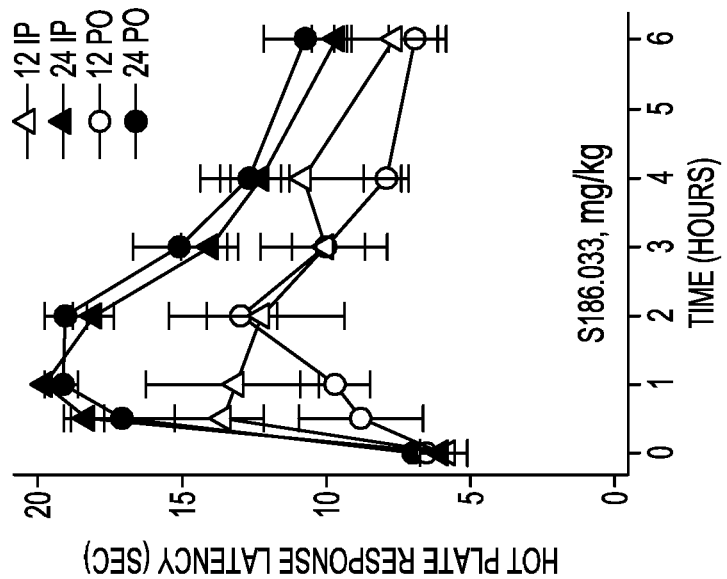
FIG. 9 shows comparative i.p. and p.o. data for compounds 5186.006 and S086.033, given at 12 mg/kg and 24 mg/mg by each mode of delivery, as indicated.
Figure 9A:
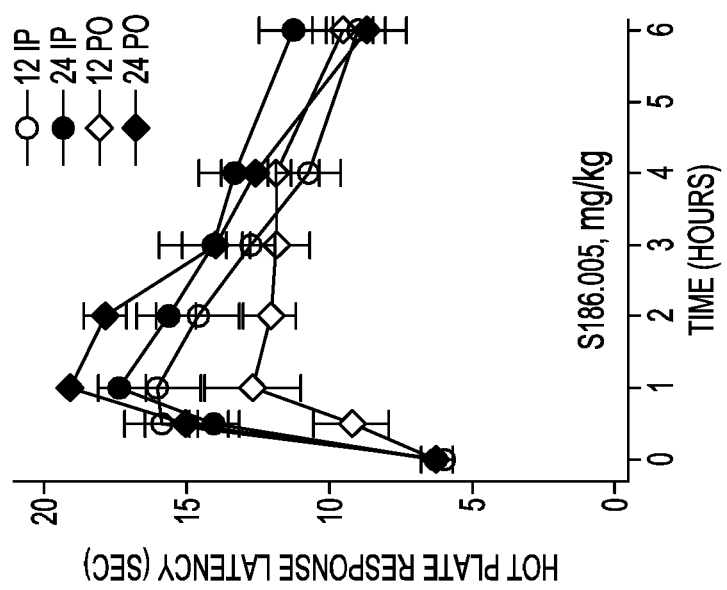

As shown above, S186.005 has significant oral bioavailability in mice (51%), as do other selected compounds of the invention (data not shown). Thus the data such as shown earlier in Example 31, analgesic potencies, expressed by area under the curve analysis, for selected compounds compared to morphine sulfate in the hot plate (52° C.) and warm water (49° C.) tail immersion (tail flick) tests following i.p. dosing may, for certain compounds of the invention, be similarly generated following p.o. dosing. Shown in FIG. 9 are comparative i.p. and p.o. data for compounds S186.006 and S086.033, given at 12 mg/kg and 24 mg/mg by each mode of delivery, as indicated. The data suggest that significant antinociception is seen at several time points following oral delivery in a mammal. Thus compounds of the invention may be administered orally, though other modes of administration common in the field may also be used.

Aspects of Compounds of the Invention as Related to Prior Art

Figure 2:
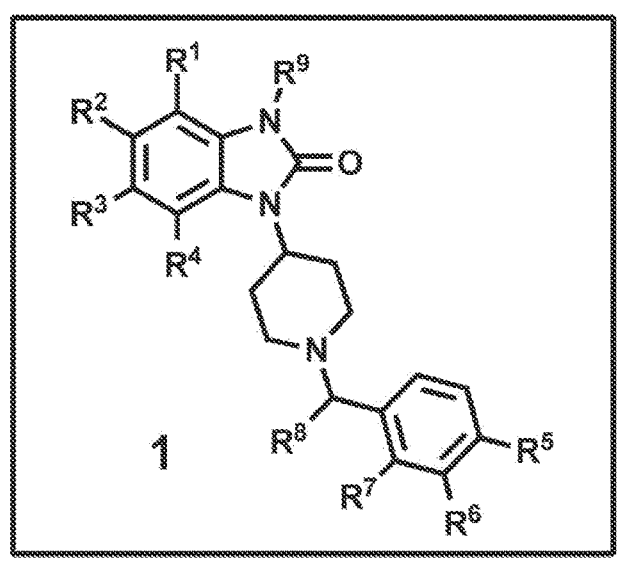
FIG. 2 depicts a generic formula of a compound of the invention as disclosed and claimed herein.

The substituents $R^1$-$R^7$ in general structure 1 (FIG. 2) are critical for obtaining claimed functionally biased MOR agonists in the indicated structural series. Many compounds in which $R^1$-$R^4$ or $R^5$-$R^7$ are all equal to hydrogen atoms (i.e., the phenyl rings are unsubstituted) are indeed MOR agonists, as would be expected based upon the findings of Janssen (30). Quite unexpectedly, however, we have found that such compounds show little or no functional bias, with G/βarr2 bias factors typically <1 (see Table 5). This table shows several specific examples of how substituents $R^1$-$R^7$ substantially and unexpectedly alter G/βarr2 bias in MOR agonists, relative to analogues without substituents in one of the phenyl rings in the core scaffold.

TABLE 5

| example | structure | GTPγS EC$_{50}$ | Bias Factor G/βarr2 ΔΔτ/KA GTPγS |
|---|---|---|---|
| 4 | (5-Cl benzimidazolone-piperidine-CH$_2$-2-F-4-Br-phenyl) | 220 nM | 9.6 |
| 5 | (5-Cl benzimidazolone-piperidine-CH(CH$_3$)-4-SEt-phenyl) (±) | 291 nM | 5.8 |
| 15 | (5,6-diCl benzimidazolone-piperidine-CH$_2$-4-Br-phenyl) | 129 nM | >10 |
| 26 | (4-Cl benzimidazolone-piperidine-CH$_2$-2-Cl-phenyl) | 36 nM | 4.0 |

| example | closely related structure | GTPγS EC$_{50}$ | Bias Factor G/βarr2 ΔΔτ/KA GTPγS |
|---|---|---|---|
| 4 | (5-Cl benzimidazolone-piperidine-CH$_2$-phenyl) | 950 nM | −0.6 |

TABLE 5-continued

| # | Structure | | |
|---|---|---|---|
| 5 | (benzimidazolone-piperidine with CH(CH3)-phenyl-SEt, racemic) | 300 nM | −0.3 |
| 15 | (benzimidazolone-piperidine-CH2-phenyl-Br) | 350 nM | −0.3 |
| 26 | (Cl-benzimidazolone-piperidine-CH2-phenyl) | 540 nM | 0.1 |

Definitions and Abbreviations

The term "GPCR" as used herein refers to a G protein-coupled receptor, which is one member of a diverse family of glycoproteins which share certain structural features. These include the existence of seven hydrophobic stretches of about 20-25 amino acids each surrounded by eight hydrophilic regions of variable length. Each of the seven hydrophobic regions is thought to form a transmembrane alpha helix and the intervening hydrophilic regions form alternately intracellularly-exposed and extracellularly-exposed loops.

The term "MOR" as used herein refers to the GPCR commonly named the mu opioid receptor.

The term "agonist" as used herein refers to a compound that activates a GPCR, causing structural changes within the receptor complex in the absence of other receptor ligand, changes that result in the propagation of receptor signaling pathways.

The term "partial agonist" as used herein refers to a compound that binds to a receptor site but does not produce the maximal effect regardless of its concentration.

The term "ligand" as used herein refers to a compound that binds at the receptor site.

The term "bias" as used here refers to the preference of a ligand to activate one signaling pathway over another as determined by dose response comparison of the ligand to a reference ligand that is used to define the potential of the assay system.

The term "reference agonist" as used here defines an agonist that produces a maximal response in the cell based assay to which all other ligands are compared.

The term "bias factor" is a mathematically derived value obtained by nonlinear regression analysis of the dose response curves fit relative to the full potential curve obtained by the reference agonist's performance between two assays. This analysis produces the relative affinity of the test compound and the relatively efficiency of coupling compared to the reference compound's performance in the system. The difference between the performance of the test compound in assay 1, normalized to the reference compound, and its performance in assay 2, normalized to the reference compound, produces the bias factor. The bias factors may diverge with different analyses. A truly biased agonist will have a bias factor that is significantly different than 1.

The term "heteroatom" as used herein refers to an atom of any element other than carbon or hydrogen. Common heteroatoms include nitrogen, oxygen, phosphorus, sulfur and selenium.

The abbreviation "CNS" as used herein refers to the central nervous system of an organism.

The term "$EC_{50}$" as used herein refers to the dose of a test compound which produces 50% of its maximum response or effect in an assay.

The term "$ED_{50}$" as used herein refers to the dose of a test compound which produces 50% of its maximum response or effect in an animal experiment.

The term "$E_{max}$" as used herein refers to the degree of the effect of a test compound in an assay (percent activation, as an example) relative to the maximum response or effect in the assay resulting from the use of a reference compound.

The term "$LD_{50}$" as used herein refers to the dose of a test compound which is lethal in 50% of test subjects in an animal experiment.

The term "structure-activity relationship" or "SAR" as used herein refers to the way in which altering the molecular structure of test compounds alters their interaction with a receptor, enzyme, etc.

The term "electron-withdrawing group" as used herein is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant.

The term "alkyl" as used herein throughout the specification, examples, and claims refers to a hydrocarbon group, and includes branched chain variations.

The term "cycloalkyl" as used herein throughout the specification, examples, and claims refers to a cyclic hydrocarbon group, and may include alkyl substituents on the cyclic hydrocarbon group.

The term "substituted alkyl" as used herein refers to alkyl moieties having substituents replacing a hydrogen atom on one or more carbon atoms of the hydrocarbon backbone. Such substituents can include, for example, a halogen, a halogenated alkyl (e.g., $CF_3$), a hydroxyl, a carbonyl, an amino, an amido, an amidine, an imine, an alkoxy, a halogenated alkoxy (e.g., $OCF3$, $OCHF2$, etc.) a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic group. It will be understood by those skilled in the art that the moieties substituted on the hydrocarbon chain can themselves be substituted, if appropriate.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names "1,2-dimethylbenzene" and "ortho, meta-dimethylbenzene" are synonymous.

The term "aralkyl" as used herein refers to an alkyl group substituted with an aryl group (e.g., an aromatic or heteroaromatic group). Examples include $CH_2Ph$, $CH_2CH_2Ph$, $CH_2CH_2$-indole, and the like. The aromatic ring can be substituted at one or more ring positions with such substituents, as described above.

The terms "alkenyl" and "alkynyl" refer to unsaturated aliphatic groups analogous in length and possible substitution to the alkyls described above, but that contain at least one double or triple bond respectively.

Unless the number of carbons is otherwise specified. "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "heterocyclyl" or "heterocyclic group" as used herein refer to 3- to 10-membered ring structures, more preferably 3- to 7-membered rings that include one to four heteroatoms. Heterocycles can also be polycycles. Heterocyclyl groups include, for example, azetidine, azepine, thiophene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF3$, —CN, or the like.

The term "carbocycle", as used herein, refers to an aromatic or non-aromatic ring in which each atom of the ring is carbon.

As used herein, the term "halogen" designates —F, —Cl, —Br or —I.

As used herein, the term "hydroxyl" means —OH.

As used herein, the term "sulfonyl" means —$SO_2$—.

The terms "amine" and "amino" as used herein are recognized in the art and refer to both unsubstituted and substituted amines, e.g., a moiety that can be represented by the general formulas —$NH2$, —NHR, —NRR", where R and R' are alkyl, cycloalkyl, aryl, or heterocyclyl groups, as example.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like.

The term "ether" as used herein refers to two hydrocarbons groups covalently linked by an oxygen atom.

Various abbreviations used herein include Me, Et, Ph, Tf, Nf, Ts, Ms and represent methyl, ethyl, phenyl, trifluoromethanesulfonyl, nonafluorobutanesulfonyl, para-toluenesulfonyl and methanesulfonyl groups, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "sulfonamido" is art recognized and includes a moiety that can be represented by the general formula —SO$_2$—N(R)(R') wherein where R, and R' are alkyl, cycloalkyl, aryl, or heterocyclyl groups, as examples.

The term "sulfonyl", as used herein, refers to a moiety that can be represented by the general formula —SO$_2$R wherein where R is an alkyl, cycloalkyl, aryl, or heterocyclyl group, as examples.

Various substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The phrase "protecting group" as used herein means temporary substituents which protect a potentially reactive functional group from undesired chemical transformations. Examples of such protecting groups include carbamates of amines, esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Additional asymmetric carbon atoms may be present in a substituent such as an alkyl group. All such isomers, as well as mixtures thereof, are intended to be included in this invention.

If a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "Example" as used herein indicates the procedures followed for the preparation of a claimed compound, In general, the compounds of the present invention may be prepared by the methods illustrated in the general reaction schemes as, for example, described in the examples, or by modifications thereof, using readily available starting materials, reagents and conventional synthesis procedures not mentioned here.

It is understood that certain claimed molecules may stably exist in with isotopic variants among specific substituents, such as deuterium or tritium in the place of hydrogen. Such isotopic variants also fall within the scope of the invention.

The term "antinociception" is defined is the blockade of the perception of a nociceptive stimulus wherein nociceptive is defined as "somatic or visceral pain processed by a normal, unaltered nervous system" (4).

The term "G protein signaling bias" refers to a calculated bias factor comparing the performance of the test compound against the performance of a reference compound in a βarrestin2 recruitment assay and a G protein coupling assay, normalized to reference standard. This is not implying that other arrestin pathways, such as that of receptor post-translational modifications or βarrestin1 recruitment, are not differentially affected. Furthermore, this does not imply the recruitment of any particular heterotrimeric G protein subunits.

In the Examples, certain abbreviations are be used for specific chemical reagents or solvents. These are defined as follows:

DMSO=dimethyl sulfoxide, or Me$_2$S—O; THF=tetrahydrofuran; TFA=trifluoroacetic acid; DMF=N,N'-dimethylformamide; triphosgene=Cl$_3$CO—CO—OCCl$_3$; Ac=acetyl=(CH$_3$C═O); HPLC=high performance liquid chromatography; LCMS=an instrument consisting of an HPLC instrument linked to a mass spectrometer.

It is understood that certain groups such as amines, carboxylates, sulfonates, etc. can bear a net overall charge. When such a group or groups are present in a "claimed compound", pharmaceutically acceptable salt forms of the structure are implicitly encompassed in the claims as well. For example, a claim for a compound with one or more amino groups present in the structure also implicitly claims all pharmaceutically acceptable salt forms, such as hydrochloride, methanesulfonyl, formate, oxalate, tartrate salts, and the like.

It is understood that certain "claimed compounds" may stably exist as hydrates or solvates. Such differing forms are also implicitly encompassed in the claims. Hydrates refer to molecules of water present in the crystal lattice. Solvates refer to molecules of a relatively benign solvent, such as ethanol, present in the crystal lattice.

It is understood that certain "claimed compounds" in any form, including as a salt, hydrate, or solvate, may stably exist in multiple solid crystalline and/or amorphous forms. Such forms may confer different physical properties (e.g., rate of dissolution, stability, hydroscopicity). Such differing solid forms are also implicitly encompassed in the claims.

DOCUMENTS CITED

1. Pasternak G W, Pan Y X. 2013. Mu opioids and their receptors: evolution of a concept. *Pharmacological reviews.* 65(4):1257-317. PMCID: 3799236.
2. Pasternak G W. 2014. Opioids and their receptors: Are we there yet?*Neuropharmacology.* 76 Pt B:198-203.
3. Cox B M. 2013. Recent developments in the study of opioid receptors. *Molecular pharmacology.* 83(4):723-8.
4. Mogil J S. 2009. Animal models of pain: progress and challenges. *Nature reviews Neuroscience.* 10(4):283-94.
5. Manglik A, Kruse A C, Kobilka T S, Thian F S, Mathiesen J M, Sunahara R K, Pardo L, Weis W I, Kobilka B K, Granier S. 2012. Crystal structure of the micro-opioid receptor bound to a morphinan antagonist. *Nature.* 485 (7398):321-6. PMCID: 3523197.
6. Williams J T, Ingram S L, Henderson G, Chavkin C, von Zastrow M, Schulz S, Koch T, Evans C J, Christie M J. 2013. Regulation of mu-opioid receptors: desensitization, phosphorylation, internalization, and tolerance. *Pharmacological reviews.* 65(1):223-54. PMCID: 3565916.

7. Urban J D, Clarke W P, von Zastrow M, Nichols D E, Kobilka B, Weinstein H, Javitch J A, Roth B L, Christopoulos A, Sexton P M, Miller K J, Spedding M, Mailman R B. 2007. Functional selectivity and classical concepts of quantitative pharmacology. *The Journal of pharmacology and experimental therapeutics.* 320(1):1-13.
8. Kenakin T. 2007. Collateral efficacy in drug discovery: taking advantage of the good (allosteric) nature of 7TM receptors. *Trends in pharmacological sciences.* 28(8): 407-15.
9. Violin J D, Lefkowitz R J. 2007. Beta-arrestin-biased ligands at seven-transmembrane receptors. *Trends in pharmacological sciences.* 28(8):416-22.
10. Bohn L M. Selectivity for G Protein or Arrestin-Meidated Signaling. In: Neve K, editor. Functional Selectivity of G Protein-Coupled Receptor Ligands: New Opportunities for Drug Discovery. 1st ed: Humana Press; 2009. p. 71-85.
11. Raehal K M, Schmid C L, Groer C E, Bohn L M. 2011. Functional selectivity at the mu-opioid receptor: implications for understanding opioid analgesia and tolerance. *Pharmacological reviews.* 63(4):1001-19. PMCID: 3186080.
12. Xiao K, Sun J, Kim J, Rajagopal S, Zhai B, Villen J, Haas W. Kovacs J J, Shukla A K, Hara M R, Hemandez M, Lachmann A, Zhao S, Lin Y, Cheng Y, Mizuno K, Ma'ayan A, Gygi S P, Lefkowitz R J. 2010. Global phosphorylation analysis of beta-arrestin-mediated signaling downstream of a seven transmembrane receptor (7TMR). *Proceedings of the National Academy of Sciences of the United States of America.* 107(34):15299-304. PMCID: 2930550.
13. Raehal K M, Bohn L M. 2014. beta-arrestins: regulatory role and therapeutic potential in opioid and cannabinoid receptor-mediated analgesia. *Handbook of experimental pharmacology.* 219:427-43.
14. Bohn L M, Gainetdinov R R, Lin F T, Lefkowitz R J, Caron M G. 2000. Mu-opioid receptor desensitization by beta-arrestin-2 determines morphine tolerance but not dependence. *Nature.* 408(6813):720-3.
15. Bohn L M, Lefkowitz R J, Caron M G. 2002. Differential mechanisms of morphine antinociceptive tolerance revealed in (beta)arrestin-2 knock-out mice. *The Journal of neuroscience: the official journal of the Society for Neuroscience.* 22(23):10494-500.
16. Bohn L M, Lefkowitz R J, Gainetdinov R R, Peppel K, Caron M G, Lin F T. 1999. Enhanced morphine analgesia in mice lacking beta-arrestin 2. *Science.* 286(5449):2495-8.
17. Bohn L M, Raehal K M. 2006. Opioid receptor signaling: relevance for gastrointestinal therapy. *Current opinion in pharmacology.* 6(6):559-63.
18. Raehal K M, Walker J K, Bohn L M. 2005. Morphine side effects in beta-arrestin 2 knockout mice. *The Journal of pharmacology and experimental therapeutics.* 314(3):1 195-201.
19. Raehal K M, Bohn L M. 2011. The role of beta-arrestin2 in the severity of antinociceptive tolerance and physical dependence induced by different opioid pain therapeutics. *Neuropharmacology.* 60(1):58-65. PMCID: 2981657
20. Bohn L M, Caron, M. G., Lin, F, Lefkowitz, R J. 2003 (filed December 1999). U.S. Pat. No. 6,528,271—"Inhibition of .beta.arrestin mediated effects prolongs and potentiates opioid receptor-mediated analgesia".
21. Bohn L M, McDonald P H. 2010. Seeking Ligand Bias: Assessing GPCR Coupling to Beta-Arrestins for Drug Discovery. *Drug discovery today Technologies.* 7(1):e37-e42. PMCID: 3014586.
22. DeWire S M, Yamashita D S, Rominger D H, Liu G, Cowan C L, Graczyk T M, Chen X T, Pitis P M, Gotchev D, Yuan C, Koblish M, Lark M W, Violin J D. 2013. A G protein-biased ligand at the mu-opioid receptor is potently analgesic with reduced gastrointestinal and respiratory dysfunction compared with morphine. *The Journal of pharmacology and experimental therapeutics.* 344(3): 708-17.
23. Soergel D G, Subach R A, Burnham N, Lark M W, James I E, Sadler B M, Skobieranda F, Violin J D, Webster L R. 2014. Biased agonism of the mu-opioid receptor by TRV130 increases analgesia and reduces on-target adverse effects versus morphine: A randomized, double-blind, placebo-controlled, crossover study in healthy volunteers. *Pain.* 155(9):1829-35.
24. Soergel D G, Subach R A, Sadler B, Connell J, Marion A S, Cowan C L, Violin J D, Lark M W. 2014. First clinical experience with TRV130: pharmacokinetics and pharmacodynamics in healthy volunteers. *Journal of clinical pharmacology.* 54(3):351-7.
25. Black J W, Leff P, Shankley N P, Wood J. 1985. An operational model of pharmacological agonism: the effect of E/[A] curve shape on agonist dissociation constant estimation. *British journal of pharmacology.* 84(2):561-71. PMCID: 1987296.
26. Groer C E, Schmid C L, Jaeger A M, Bohn L M. 2011. Agonist-directed interactions with specific beta-arrestins determine mu-opioid receptor trafficking, ubiquitination, and dephosphorylation. *The Journal of biological chemistry.* 286(36):31731-41. PMCID: 3173119.
27. Kenakin T, Watson C, Muniz-Medina V, Christopoulos A. Novick S. 2012. A simple method for quantifying functional selectivity and agonist bias. *ACS chemical neuroscience.* 3(3):193-203. PMCID: 3369801.
28. Schmid C L, Streicher J M, Groer C E, Munro T A, Zhou L, Bohn L M. 2013. Functional selectivity of 6'-guanidinonaltrindole (6'-GNTI) at kappa-opioid receptors in striatal neurons. *The Journal of biological chemistry.* 288 (31):22387-98. PMCID: 3829329.
29. Zhou L, Lovell K M, Frankowski K J, Slauson S R, Phillips A M, Streicher J M, Stahl E, Schmid C L, Hodder P, Madoux F, Cameron M D, Prisinzano T E, Aube J, Bohn L M. 2013. Development of functionally selective, small molecule agonists at kappa opioid receptors. *The Journal of biological chemistry.* 288(51):36703-16. PMCID: 3868780.
30. Janssen P A. 1967. Derivatives of benzimidazolinyl piperidine, U.S. Pat. No. 3,318,900.
31. Teranishi Mea. 1983. Novel piperidine derivatives and pharmaceutical compositions containing same, EP0092391.
32. Den Hartog JAGea. 2005. Benzimidazolone and quinazolinone derivatives as agonists on human ORL1 receptors, WO 2005/028466.
33. Patel V, Bhatt N, Bhatt P, Joshi H D. 2014. Synthesis and pharmacological evaluation of novel 1-(piperidin-4-yl)-1H-benzo[d]imidazol-2(3H)-one derivatives as potential antimicrobial agents. *Med Chem Res.* 23(4):2133-9.
34. Lipinski C A. 2004. Lead- and drug-like compounds: the rule-of-five revolution. *Drug discovery today Technologies.* 1 (4):337-41.
35. Pajouhesh H. Lenz G R. 2005. Medicinal chemical properties of successful central nervous system drugs.

NeuroRx: the Journal of the American Society for Experimental NeuroTherapeutics. 2(4):541-53. PMCID: 1201314.

All patents and publications referred to herein are incorporated by reference herein to the same extent as if each individual publication was specifically and individually indicated to be incorporated by reference in its entirety.

What is claimed is:

1. A compound of structure 1

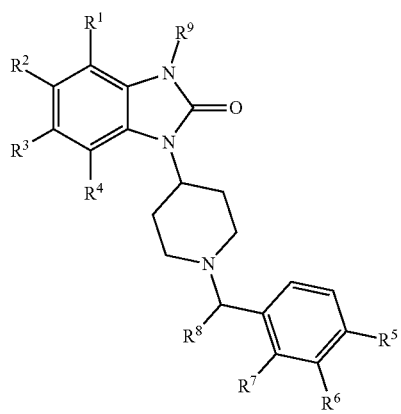

with substituents R¹-R⁹, specified as follows:
- R¹, R², R³, and R⁴ are each independently H, Cl, Br, F, OCF₃, Me, or lower alkyl, provided that one or more of groups R¹-R⁴ is not a hydrogen atom;
- R⁵ is H, Cl, Br, F, Me, CF₃, OCF₃, OCHF₂, OCH₂F, OMe, O-alkyl, SMe, S-alkyl, NH-acyl, or N(Me)-acyl;
- R⁶ is H, Cl, Br, F, Me, Et, lower alkyl, CF₃, OCF₃, OCHF₂, OCH₂F, OMe, O-alkyl, SMe, S-alkyl, NH-acyl, or N(Me)-acyl
  wherein when R⁵ and R⁶ both are O-alkyl they may be connected together in a ring of 5-7 atoms by 1-3 CH₂ groups;
- R⁷=Cl, Br, F, Me, CF₃, OCF₃, OCHF₂, or OCH₂F; provided that one or more of groups R⁵-R⁷ is also not a hydrogen atom;
- R⁸=H, Me, or Et; and
- R⁹=H, Me, Et, lower alkyl, or CH₂-cycloalkyl;

or, where a chiral carbon is present, an R-enantiomer, S-enantiomer, or racemic mixture thereof;
and/or a pharmaceutically acceptable salt thereof.

2. A compound selected from any of the following compounds or, where a chiral carbon is present, an R-enantiomer, S-enantiomer, or racemic mixture thereof: and/or a pharmaceutically acceptable salt thereof:

1

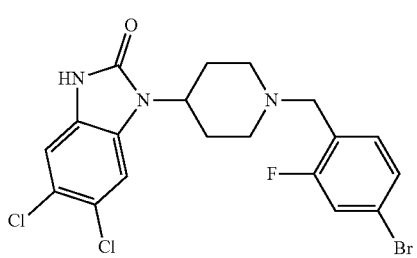

2

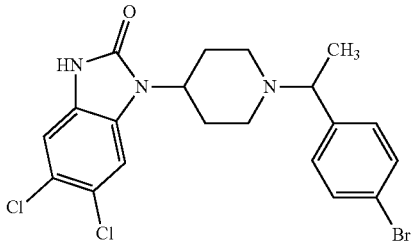

3

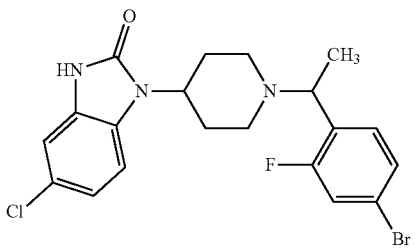

4

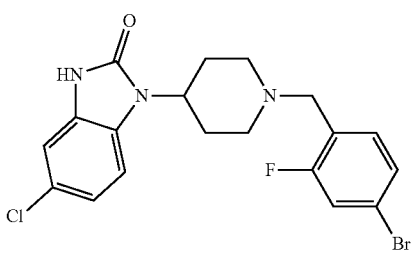

5

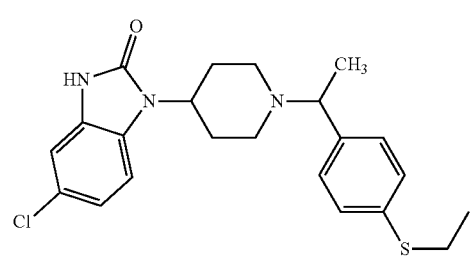

6

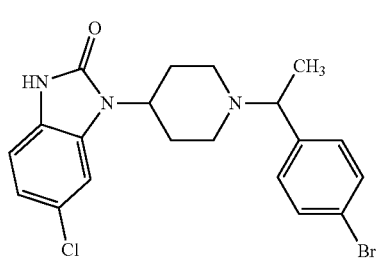

7

8
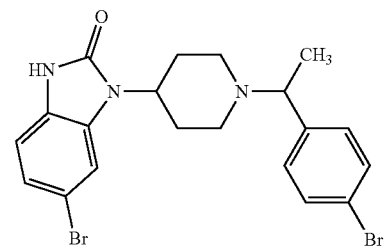
9
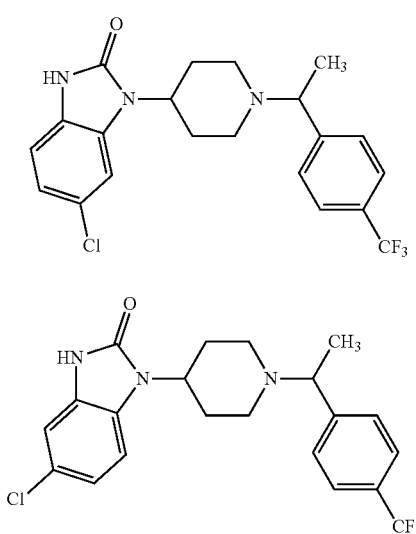
10
11
12
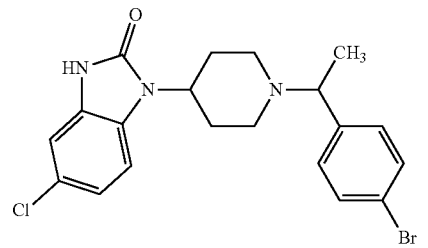
13
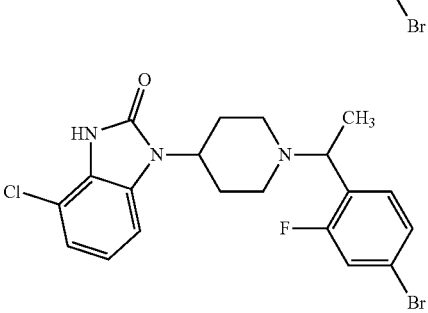
14
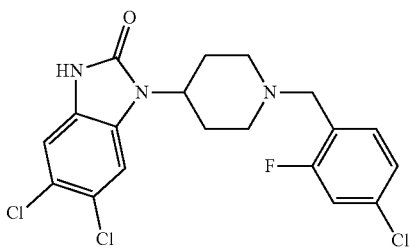
15
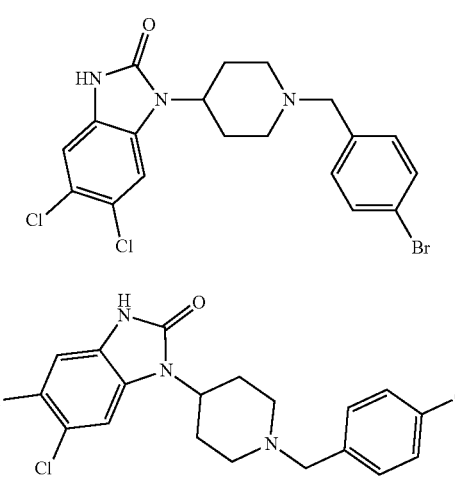
16
17
18
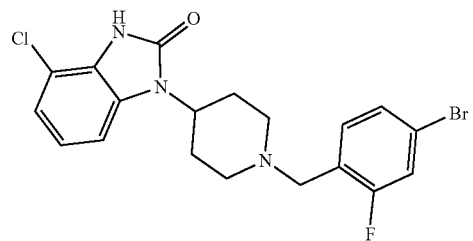
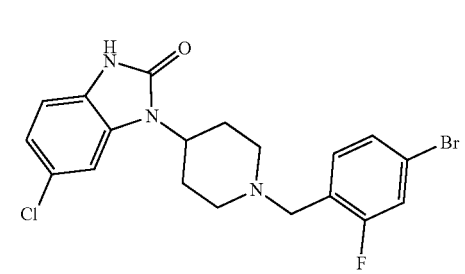
19
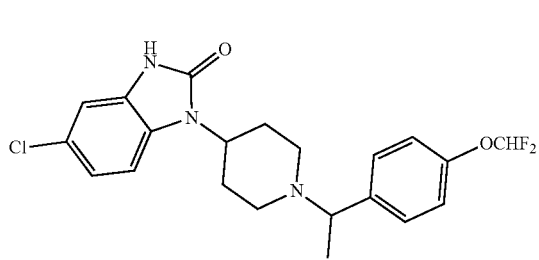

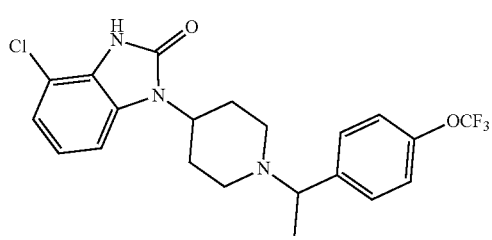

20

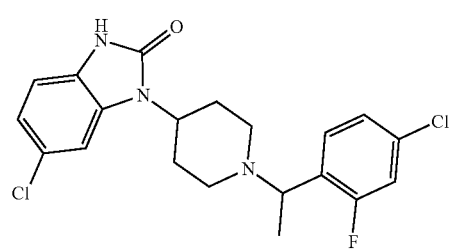

21

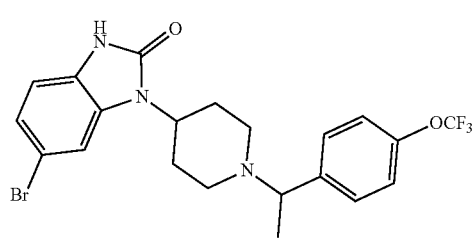

22

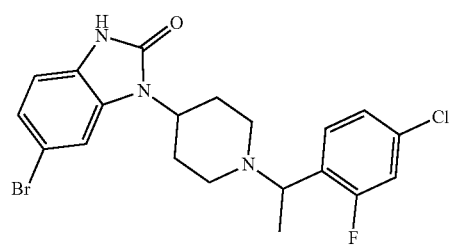

23

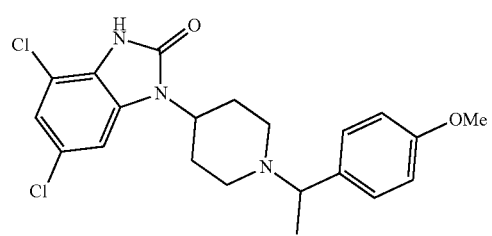

24

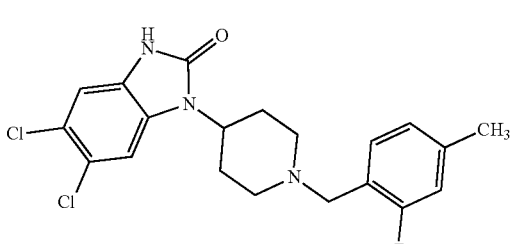

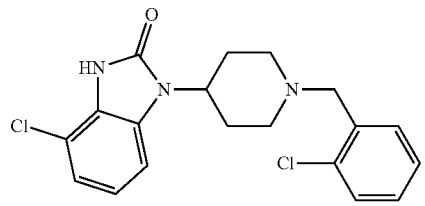

26

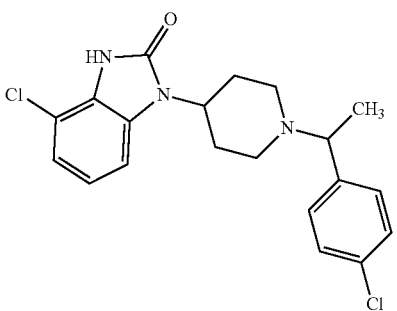

27

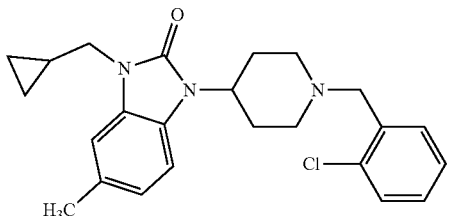

28

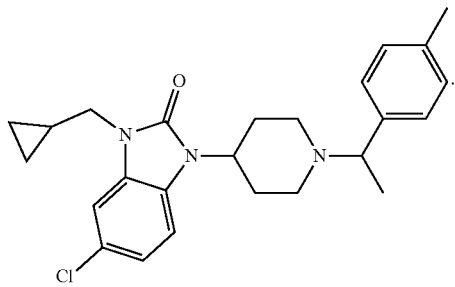

29

3. A pharmaceutical composition comprising a compound or, where a chiral carbon is present, an R-enantiomer, S-enantiomer, or racemic mixture thereof, and/or a or pharmaceutically acceptable salt thereof of claim 1 or 2 and a pharmaceutically acceptable excipient.

4. The compound or pharmaceutically acceptable salt thereof according to claim 1 or 2, wherein when a chiral carbon is present, the compound is a racemate.

5. The compound or pharmaceutically acceptable salt thereof according to claim 1 or 2, wherein when a chiral carbon is present, the compound is the R-enantiomer.

6. The compound or pharmaceutically acceptable salt thereof according to claim 1 or 2, wherein when a chiral carbon is present, the compound is the S-enantiomer.

\* \* \* \* \*